United States Patent [19]

Scribner

[11] 4,320,136
[45] Mar. 16, 1982

[54] 8-AZA-16,16-DIFLUOROPROSTANOIDS

[75] Inventor: Richard M. Scribner, Wilmington, Del.

[73] Assignee: E. I. Du Pont de Nemours and Company, Wilmington, Del.

[21] Appl. No.: 176,784

[22] Filed: Aug. 11, 1980

[51] Int. Cl.³ .................... A61K 31/40; C07D 207/27
[52] U.S. Cl. ............................. 424/274; 260/326.43; 260/946; 542/442
[58] Field of Search .................. 260/326.43; 424/274; 542/442

[56] References Cited

U.S. PATENT DOCUMENTS

| | | | |
|---|---|---|---|
| 3,873,566 | 3/1975 | Scribner | 424/273 P |
| 3,962,293 | 6/1976 | Magerlein | 260/408 |
| 3,969,376 | 7/1976 | Magerlein | 260/408 |
| 3,969,377 | 7/1976 | Magerlein | 260/408 |
| 3,969,378 | 7/1976 | Magerlein | 260/408 |
| 3,969,379 | 7/1976 | Magerlein | 260/408 |
| 3,969,380 | 7/1976 | Magerlein | 260/408 |
| 3,969,381 | 7/1976 | Magerlein | 260/408 |
| 3,974,189 | 8/1976 | Magerlein | 260/408 |
| 3,974,190 | 8/1976 | Magerlein | 260/408 |
| 3,974,191 | 8/1976 | Magerlein | 260/408 |
| 3,974,192 | 8/1976 | Magerlein | 260/408 |
| 3,974,193 | 8/1976 | Magerlein | 260/408 |
| 3,975,399 | 8/1976 | De Franco et al. | 424/244 |
| 4,003,911 | 1/1977 | Scribner | 424/274 |
| 4,017,534 | 4/1977 | Schaub et al. | 260/468 D |
| 4,032,533 | 6/1977 | Scribner | 424/270 |
| 4,113,873 | 9/1978 | Himizu et al. | 424/274 |
| 4,115,401 | 9/1978 | Nanthavong et al. | 260/326.43 |
| 4,177,346 | 12/1979 | Nelson | 542/427 |
| 4,187,381 | 2/1980 | Holland et al. | 560/121 |
| 4,211,876 | 7/1980 | Scribner | 548/367 |

FOREIGN PATENT DOCUMENTS 854268 5/1977 Belgium .
2619638 11/1977 Fed. Rep. of Germany .

OTHER PUBLICATIONS

Himizu et al. Chem. Abst., vol. 87, 1977, 87:68139d.
Magerlein et al. Prostaglandins 9 (4) pp. 527–529, 1975.
Fieser et al. Advanced Organic Chemistry pp. 84–89.
Cram & Hammond 2nd Edition, Organic Chemistry, McGraw-Hill, pp. 174–176.

Primary Examiner—Henry R. Jiles
Assistant Examiner—Jane T. Fan
Attorney, Agent, or Firm—James A. Costello

[57] ABSTRACT

Biologically active 8-aza-16,16-difluoroprostanoids having the formula:

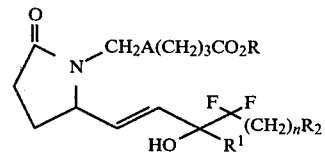

wherein
A is CH=CH (cis or trans), C≡C, or $CH_2CH_2$;
R is H, $C_1$–$C_{12}$ n-alkyl, branched chain alkyl, or cycloalkyl, or a physiologically acceptable metal or amine salt cation;
$R^1$ is H, $CH_3$, or $C_2H_5$;
$R^2$ is $CH_3$, $CF_3$, phenyl, or mono- or disubstituted phenyl, the phenyl substituents being selected from the group F, Cl, $CH_3$, $OCH_3$, $NO_2$, and $CF_3$;
n is an integer from 3 to 8 when $R^2$ is $CH_3$ or $CF_3$, or from 0 to 2 when $R^2$ is phenyl or substituted phenyl;
as racemic stereo isomer mixtures, or single or mixed optically-active stereo isomers.

37 Claims, No Drawings

8-AZA-16,16-DIFLUOROPROSTANOIDS

BACKGROUND OF THE INVENTION

1. Field of the Invention

This invention concerns biologically active 8-aza-16,16-difluoroprostanoids which can also be classified as difluoro-1,5-disubstituted-2-pyrrolidones.

2. State of the Art

There are many references in the literature to prostanoids, a term which is generic to natural and synthetic prostaglandins and prostaglandin-like compounds. It is well known in connection with these prostanoids that even slight differences in chemical structures or stereochemical configurations will have profound effects on biological activity.

Prostanoids have a five-membered ring bearing relatively lengthy substituents on adjacent ring atoms. In most of the known prostanoids, the rings are carbocyclic; in a few of these compounds one of the side chains is substituted in the C-16 position by two fluorine atoms. Representative of the publications which disclose carbocyclic-based 16,16-difluoroprostanoids are: Belgium Pat. No. 817,846 (Magerlein), U.S. Pat. No. 4,017,534 (Schaub et al), U.S. Pat. No. 4,187,381 (Holland et al), and Magerlein et al, *Prostaglandins,* 9 (4) 527 to 529 (1975).

Representative of heterocycle-based prostanoids are the aza- and diaza-prostanoids disclosed in these publications: U.S. Pat. No. 3,873,566 (Scribner), U.S. Pat. No. 3,975,399 (De Franco and Scribner), U.S. Pat. No. 4,003,911 and U.S. Pat. No. 4,032,533 (Scribner), U.S. Pat. No. 4,113,873 (Himizu), U.S. Pat. No. 4,177,346 (Nelson), U.S. Pat. No. 4,211,876 (Scribner), and Belgium Pat. No. 854,268 (Hoechst).

The prostanoids now described differ from those disclosed in these publications in that they combine all of the following structural features (designated by conventional prostanoid numbering): (a) a single nitrogen atom at position 8 in a heterocyclic five-membered ring; (b) a carbonyl group in the five-membered ring at position 9 (making them lactams); (c) (trans) double bonds between carbons C-13 and C-14 of the C-15 hydroxyl-bearing side chains (making them allylic alcohols); (d) two fluorine atoms at C-16 of the hydroxyl-bearing side chain. In addition to all of the above characteristics, many of the compounds of this invention are optically-active having one predominant configuration (R or S) at carbon atom C-12 and some have phenyl or substituted-phenyl groups attached at the end of the C-15 hydroxyl-bearing side chain. For example, the compounds now described differ from the optically-active lactams of the Nelson reference in that they contain fluorine atoms (at C-16) and they differ from compounds of Scribner (U.S. Pat. No. 4,003,911) in that they are allylic alcohols having lactam carbonyl groups at C-9 rather than saturated alcohols with ketone carboxyl groups at C-9. It is the combination of structural features outlined above which invests the compounds of this invention with their unusual and useful biological properties.

SUMMARY OF THE INVENTION

The compounds of this invention have the formula

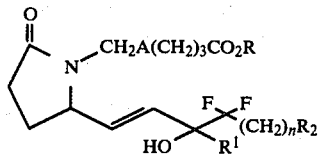

wherein
A is CH=CH (cis or trans), C≡C, or $CH_2CH_2$;
R is H, $C_1$–$C_{12}$ n-alkyl, branched chain alkyl, or cycloalkyl, or a physiologically acceptable metal or amine salt cation;
$R^1$ is H, $CH_3$ or $C_2H_5$;
$R^2$ is $CH_3$, $CF_3$, phenyl, or mono- or disubstituted phenyl, the phenyl substituents being selected from the group F, Cl, $CH_3$, $OCH_3$, $NO_2$, and $CF_3$;
n is an integer from 3 to 8 when $R^2$ is $CH_3$ or $CF_3$, or from 0 to 2 when $R^2$ is phenyl or substituted phenyl.

The compounds of this invention can be prepared as either (i) a racemic mixture of stereo isomers,
(ii) an optically active mixture of stereo isomers, or
(iii) a single optically pure stereo isomer.

It is to be understood that by "single optically pure stereo isomer" is meant a substantially pure single optical isomer having little or no other stereo isomer present.

This invention also concerns a two-step process for preparing dialkyl-3,3-difluoro-2-oxoalkyl phosphonates, wherein the alkyl of the dialkyl moiety has from 1 to 4 carbon atoms and n and $R^2$ are as previously defined. The process comprises reacting diethylaminosulfur trifluoride with an alkyl-2-oxoalkanoate, either neat or in an inert solvent, at about 0° to 50° C. to form alkyl-2,2-difluoroalkanoate which is then reacted with a salt of dimethyl methyl phosphonate, most appropriately in an inert solvent such as tetrahydrofuran (THF), ethylene glycol dimethyl ether (glyme) or the like.

This invention also concerns a process for preparing 8-aza-16,16-difluoro-15-oxoprostanoids comprising reacting a phosphonate intermediate described above with tert-butyl 7-(2-oxo-5-formylpyrrolidinyl)heptanoate in an inert solvent. The phosphonate is preferably a 3,3-difluoro-2-oxononyl phosphonate, or a 3,3-difluoro-2-oxo-3-phenylpropyl phosphonate. The compounds of this invention can then be prepared by reducing the oxo group at position 15 to a hydroxy group.

This invention also concerns pharmaceutical compositions containing the described compounds as active ingredient. These pharmaceutical compositions are typically in tablet, capsule, injectable or aerosol form. This invention also concerns a method for preventing or treating in a human or animal subject peptic ulcer, including gastric and duodenol ulcer; blocking or reversing gastrointestinal ulcerative change induced by a nonsteroidal antiinflammatory drug; preventing or treating inflammatory bowel disease such as colitis; and for controlling the symptoms of bronchial asthma, in each case by administering an effective amount of a pharmaceutical composition comprising the 8-aza-16,16-difluoroprostanoids of this invention. Additional details concerning pharmaceutical use will be found in the "Utility" description hereafter.

The amount of active ingredient, 8-aza-16,16-difluoroprostanoids, in each treatment dosage will vary depending upon the potency of the particular compound, the illness being treated, the weight and general condition of the subject as well as other factors readily appreciated by one skilled in the art. In general, doses from 1 μg to 500 mg can be used. Consistent with this explanation of several of the more important factors to be considered in determining the amount of active ingredient to be administered, the term "effective amount" will be employed to indicate the amount employed after an evaluation of all relevant factors.

DETAILS OF THE INVENTION

Synthesis of the compounds of this invention in optically active forms (ii) or (iii) begins with reactants in optically active forms (ii) or (iii). Racemic forms of the compounds of this invention are isolated as products of reactions of racemic starting materials. The preparation of these forms is described in more detail in the Examples. The general reaction sequence is as follows with Compounds VI, VII, VIII, X and XI being compounds of the invention:

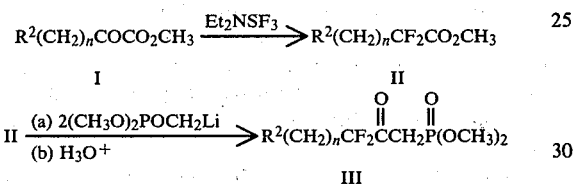

The 2-oxo-acid methyl esters I are made by any of several different general methods described in the literature for the synthesis of 2-oxoalkanoic acids or 2-oxophenylalkanoic acids and their esters; see, for example, Vogel et al, *Helv. Chimica Acta.*, 33, 116 (1950), footnote No. 2. The methods of Adickes et al, *Ann.*, 555, 48 (1944) and Schreiber, *Bull Soc. Chem. France*, 1956, 136, which involve the Claisen condensation of esters, $R^2(CH_2)_nCO_2Et$, with diethyl oxalate in the presence of sodium methoxide or NaH followed by hydrolysis and decarboxylation are convenient. The 2-oxo acids, $R^2(CH_2)_nCOCO_2H$, are conveniently converted to the corresponding methyl esters by the action of diazomethane to give 2-oxo esters I. Reaction of phenyl or substituted-phenylmagnesium halides, or the corresponding aryl lithium compounds, with dimethyloxalate gives the ω-phenyl or substituted phenyl 2-oxophenylalkanoic acid methyl esters directly. Other routes to 2-oxophenyl and 2-oxo-substituted phenyl alkanoic acids are well known in the literature, e.g., Cordier, *Pharm. Weekblad*, 93, 55 (1958); Hartzler, *J. Am. Chem. Soc.*, 81, 2024 (1959), ibid 83, 4990 (1961); Anatol et al., *C. R. Acad. Sci.*, Ser. C, 272 (12) 1157 (1971).

Esters I are treated with diethylaminosulfur trifluoride [Middleton, U.S. Pat. No. 3,976,691 (1976)], either neat or in a solvent such as methylene chloride. The methyl 2,2-difluoroalkanoates or 2,2-difluorophenylalkanoates or 2,2-difluoro-substituted phenylalkanoates thus obtained are treated with 2 molar equivalents of the lithium salt of dimethyl methyl phosphonate giving the fluorophosphonates III. Good yields in this reaction appear to depend on carrying it out at low temperature for a short time, e.g., about 10 minutes at −75°. A difluoro phosphonate ester of type III ($R^2=H$, $n=4$) has been described in the literature [Magerlein et al, *Prosta-*

*glandins*, 9 (4), 527 (1975)] as having also been prepared by reaction of ethyl α,α-difluorohexanoate with dimethyl methylphosphonate. However, the difluoro ester was described as having been prepared using the action of $MoF_6 \cdot BF_3$ on the 2-oxo ester. Diethylaminosulfur trifluoride is preferred for synthesis of the α,α-difluoroesters II from the corresponding 2-oxo esters I.

The reaction sequence then proceeds as follows, (racemic) Compounds IV being prepared as described in detail in De Franco and Scribner, U.S. Pat. No. 3,975,399 (Example 1, Parts A and B):

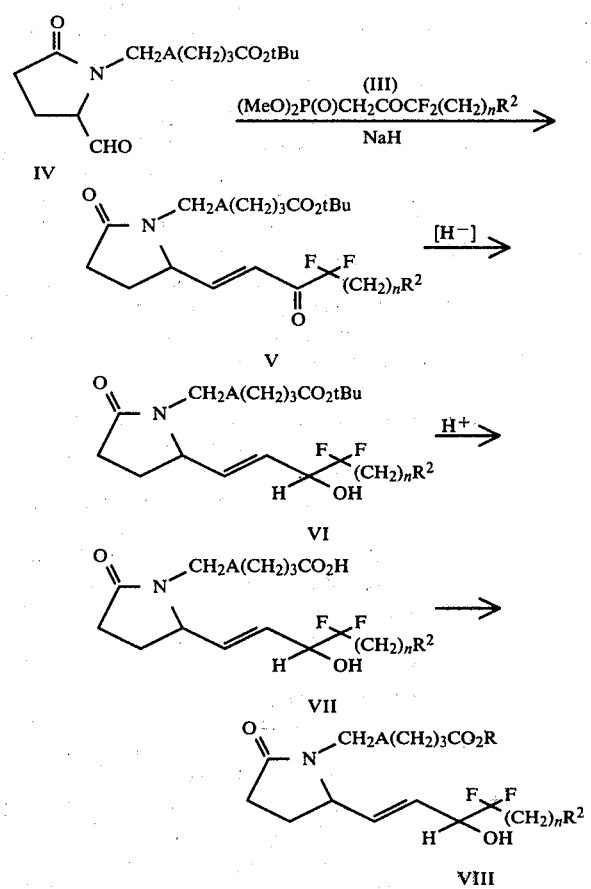

Sodium hydride can be employed to generate the sodium salt of phosphonate III. Ketones V, which can be called 8-aza-16,16-difluoro-15-oxoprostanoids, can be reduced by any of a variety of reducing agents, e.g., NaBH$_4$, zinc borohydride, and the like. Hydrolysis of the tert-butyl esters VI with 85% H$_3$PO$_4$ is convenient but hydrolysis by trifluoroacetic acid or HCl in CHCl$_3$ can also be used to obtain acids VII.

Acids VII can then be converted to the corresponding esters VIII by the action of diazoalkanes, RN$_2$, or by any of several conventional methods commonly used in organic chemistry for the conversion of carboxylic acids to esters, e.g., by reaction of the acids with the appropriate N,N-dimethylformamide dialkyl acetals [(CH$_3$)$_2$NCH(OR)$_2$], or by reaction of the sodium or silver salts of acids VII with the alkyl halides, RX (X is bromo or iodo), in an organic solvent, e.g., N,N-dimethylformamide. The salts of acid VIII, including those where R is Na, Li, K or Ca can be made by conventional acid-base reactions between one equivalent of acid VII and one equivalent of the metal hydroxide or oxide in a protic solvent such as methanol.

Ketones V can also be hydrolyzed to the keto acids IX by trifluoroacetic acid or HCl in CHCl₃, but 85% phosphoric acid is more convenient. Keto acids IX are useful as precursors to the 15-substituted 8-aza-16,16-difluoroprostanoid acids X and the corresponding esters XI. This reaction sequence is as follows:

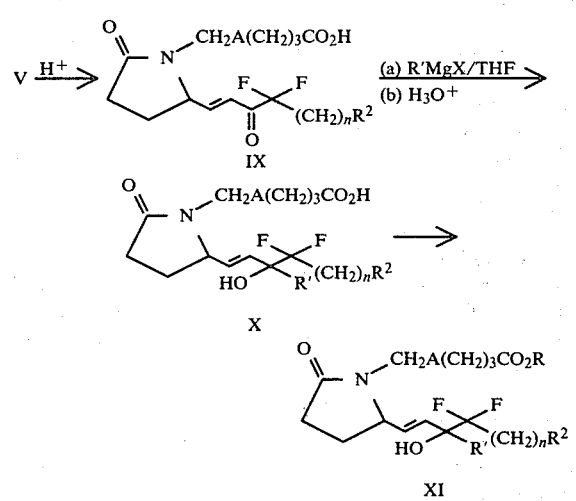

Addition of at least 2 molar equivalents of Grignard reagent, R'MgX (where R'=CH₃ or C₂H₅ and X=chloro, bromo, or iodo), to each molar equivalent of the keto acids IX in a solvent such as tetrahydrofuran followed by acidification with a weak acid (an aqueous solution saturated with NH₄Cl is convenient) gives the 15-substituted 16,16-difluoro-8-azaprostanoids X; treatment of these compounds with diazoalkanes, RN₂ (e.g., with diazoethane), or with RX or (CH₃)₂NCH(OR)₂ as described above for the conversion of VII to VIII, gives the esters XI.

As pointed out above, optically active 8-aza-16,16-difluoro prostanoids VIII and XI are made by a procedure analogous to that described above starting with optically active aldehydes IV-d or l. Optically active aldehydes IV-d or l are prepared by resolution of the esters XVI via the d or l α-methylbenzylamine salts of the corresponding acids XVII.

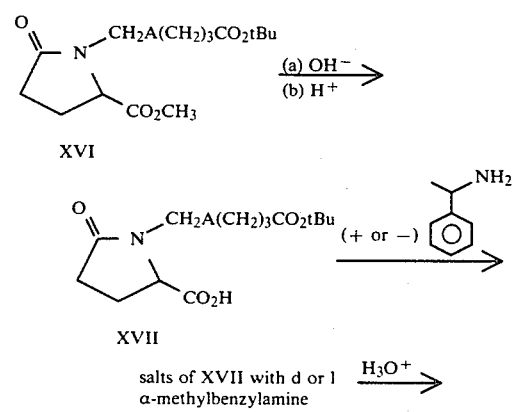

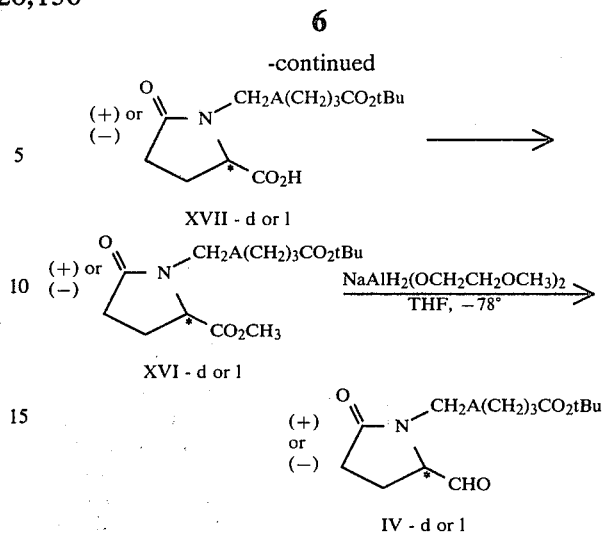

A typical preparation of racemic esters XVI is as follows: Into a dry 500 ml flask filled with dry nitrogen is placed 5.0 g of 57% sodium hydride/oil dispersion (2.85 g of sodium hydride, 0.120 mole). The dispersion is washed three times with 10 ml portions of dry petroleum ether, then dried under a nitrogen stream. To the dry hydride is added 200 ml of dimethylformamide (distilled from calcium hydride, stored over 4 A molecular sieves) with stirring (magnetic spinbar). To the suspension is added dropwise over 15 minutes a mixture of 16.0 g of methyl pyroglutamate (0.112 mole) and 28.0 g of tert-butyl 7-bromoheptanoate (0.105 mole) in 30 ml of dry dimethylformamide. After the addition is complete, the mixture is left to stir at ambient temperature for about 36 hours. The reaction mixture is poured into a well-stirred mixture of 1200 ml of water and 300 ml of diethyl ether, separated, and the aqueous phase extracted twice more with 200-ml portions of ether. The ethereal extracts are combined, washed three times with 300-ml portions of water, once with 200 ml of saturated sodium chloride solution and dried over magnesium sulfate/calcium sulfate. Removal of the ether (rotary evaporator) gives 28.8 g of a light yellow oil, which is distilled (short-path apparatus) at 152°–155°/0.3 μHg to yield 26.2 g (76%) of XVI as a colorless oil.

Esters XVI can be hydrolyzed to the corresponding racemic acids XVII and the acids resolved via their salts with d or l amines, such as d or l α-methylbenzylamine. The resolved acids XVII-d or l are converted to the corresponding methyl esters XVI-d or l with diazomethane or by any of a number of mild (non-racemizing) esterification methods known in the art, e.g., by the action of methyl iodide in the silver salts of resolved acids XVII-d or l. These methyl esters are then conveniently reduced with sodium bis(2-methoxyethoxy) aluminum hydride to the resolved aldehydes IV d or l.

The asterisks in these structures are intended to designate chiral carbon atoms that exist, by virtue of some resolution step, in one or predominantly one of two possible absolute configurations. For example, the asterisk in structure XVI-d or l indicates that the compound exists, depending on whether it is in the d (dextrorotatory) or l (levarotatory) form, in one or predominantly one of these two configurations:

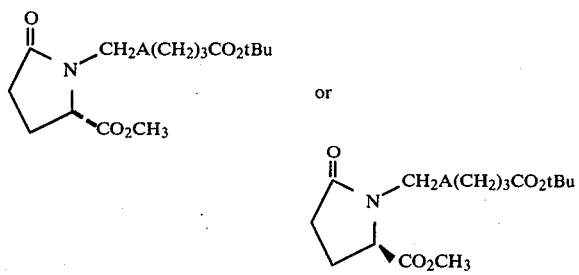

Compounds having chiral carbon atoms in one, or predominantly one, configuration are referred to as being "optically active" because at certain wavelengths such compounds rotate the plane of plane-polarized light. Generally, the sign and magnitude of the optical rotation will depend on the particular compound and the wavelength of light used for measurement of optical rotation; to a lesser degree it will also depend on solvent, concentration, and temperature. The racemic 8-azaprostanoids described in U.S. Pat. No. 3,975,399 do not have these optical properties.

The 8-aza-16,16-difluoroprostanoids made by the processes outlined above are illustrated by the structures in Columns I, J, K and L. As mentioned, asterisks indicate that these compounds are optically active owing to the fact that the C-12 carbon atoms are of one or predominantly one, of the two possible configurations. Also each structure can be a mixture of two stereo isomers epimeric at C-15, or each structure can represent one of four possible optically pure stereo isomers, prepared from optically active esters (XVI-d or l) as described above and then separated from the other C-15 epimer by chromatography or by fractional crystallization. Racemic compounds corresponding to those represented in Columns I, J, K and L can also be made by analogous processes using as starting materials racemic esters XVI instead of resolved esters XVI-d or l.

Specific reactants and products illustrating the general reactions of I, II, III . . . etc. above are listed in Columns A to L. Compounds identified by the same lower case letter (a, b, c, etc.) belong to the same series of reactions. For example, the 2-oxoester (a) of Column A affords 2,2-difluoro ester (a) of Column B on treatment with $Et_2NSF_3$; the latter affords the fluorophosphonate ester (a) of Column C. Resolved ester (a) of Column D is reduced by $NaAlH_2$ ($OCH_2CH_2OCH_3$) to give aldehyde (a) of Column E, and this on treatment with the fluorophosphonate (a) of Column C gives the fluoroketone (a) of Column F. This fluoroketone can be hydrolyzed to the acid (a) of Column G, which in turn on treatment with methylmagnesium chloride (Column H), gives the 8-aza-15-methyl-16,16-difluoro-prostanoid (a) of Column K. This acid can be converted to amine salt (a) of Column L.

The $\omega,\omega,\omega$-trifluoro-2-oxoesters of Column A are prepared by conventional synthetic methods. The fluorinating reagent sulfur tetrafluoride [Boswell et al, *Organic Reactions*, 21, 1 (1974)] is useful for preparing such compounds, e.g., by the following sequence of reactions.

| Column A (I) | Column B (II) |
|---|---|
| (a) $CH_3(CH_2)_3COCO_2CH_3$ | (a) $CH_3(CH_2)_3CF_2CO_2CH_3$ |
| (b) $CH_3(CH_2)_3COCO_2CH_3$ | (b) $CH_3(CH_2)_3CF_2CO_2CH_3$ |
| (c) $CF_3(CH_2)_3COCO_2CH_3$ | (c) $CF_3(CH_2)_3CF_2CO_2CH_3$ |
| (d) $CH_3(CH_2)_4COCO_2CH_3$ | (d) $CH_3(CH_2)_4CF_2CO_2CH_3$ |
| (e) $CH_3(CH_2)_5COCO_2CH_3$ | (e) $CH_3(CH_2)_5CF_2CO_2CH_3$ |
| (f) $CH_3(CH_2)_5COCO_2CH_3$ | (f) $CH_3(CH_2)_5CF_2CO_2CH_3$ |
| (g) $CF_3(CH_2)_6COCO_2CH_3$ | (g) $CF_3(CH_2)_6CF_2CO_2CH_3$ |
| (h) $CF_3(CH_2)_6COCO_2CH_3$ | (h) $CF_3(CH_2)_6CF_2CO_2CH_3$ |
| (i) $CH_3(CH_2)_7COCO_2CH_3$ | (i) $CH_3(CH_2)_7CF_2CO_2CH_3$ |
| (j) $CH_3(CH_2)_8COCO_2CH_3$ | (j) $CH_3(CH_2)_8CF_2CO_2CH_3$ |
| (k) 3-Cl-C₆H₄-COCO₂CH₃ | (k) 3-Cl-C₆H₄-CF₂CO₂CH₃ |
| (l) 3-CF₃-C₆H₄-CH₂COCO₂CH₃ | (l) 3-CF₃-C₆H₄-CH₂CF₂CO₂CH₃ |
| (m) 3-F, 4-CH₃-C₆H₃-CH₂COCO₂CH₃ | (m) 3-F, 4-CH₃-C₆H₃-CH₂CF₂CO₂CH₃ |
| (n) 4-O₂N, 3-OCH₃-C₆H₃-CH₂CH₂COCO₂CH₃ | (n) 4-O₂N, 3-OCH₃-C₆H₃-CH₂CH₂CF₂CO₂CH₃ |

| Column C (III) | Column D (XVI - d or l) |
|---|---|
| (a) $(CH_3O)_2P(O)CH_2COCF_2(CH_2)_3CH_3$ | (a) pyrrolidinone with N-$(CH_2)_6CO_2tBu$ and $*CO_2CH_3$ |

-continued
(b) $(CH_3O)_2P(O)CH_2COCF_2(CH_2)_3CH_3$  (b) 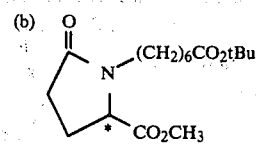
(c) $(CH_3O)_2P(O)CH_2COCF_2(CH_2)_3CF_3$  (c) 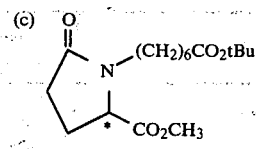
(d) $(CH_3O)_2P(O)CH_2COCF_2(CH_2)_4CH_3$  (d) 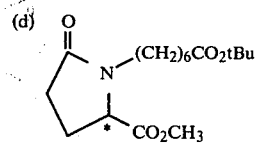
(e) $(CH_3O)_2P(O)CH_2COCF_2(CH_2)_5CH_3$  (e) 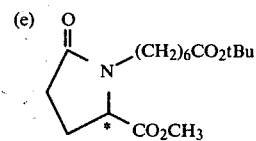
(f) $(CH_3O)_2P(O)CH_2COCF_2(CH_2)_5CH_3$  (f) 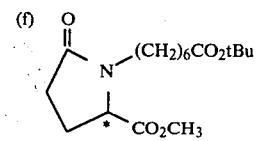
(g) $(CH_3O)_2P(O)CH_2COCF_2(CH_2)_6CF_3$  (g) 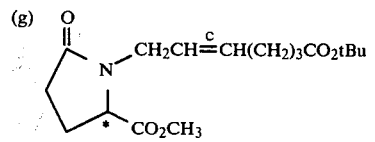
(h) $(CH_3O)_2P(O)CH_2COCF_2(CH_2)_6CF_3$  (h) 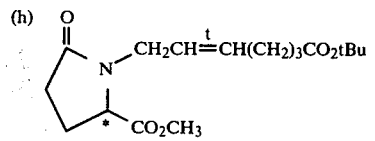
(i) $(CH_3O)_2P(O)CH_2COCF_2(CH_2)_7CH_3$  (i) 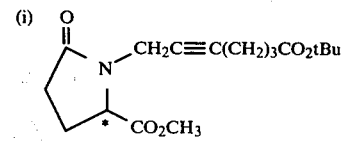
(j) $(CH_3O)_2P(O)CH_2COCF_2(CH_2)_8CH_3$  (j) 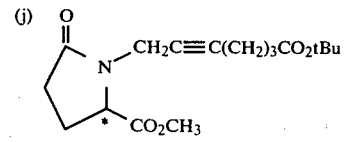
(k) 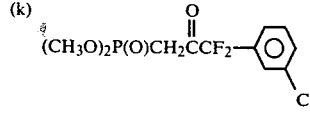  (k) 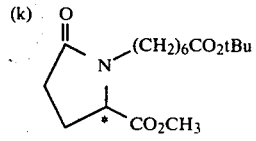
(l) 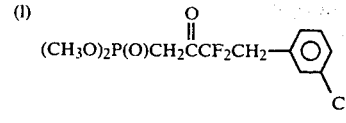  (l) 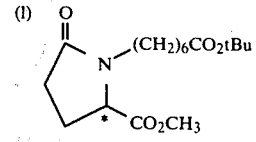
(m) 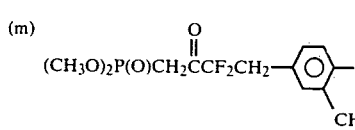  (m) 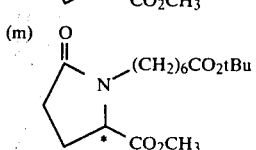

-continued
(n) 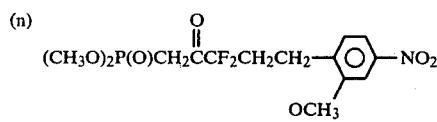
(n) 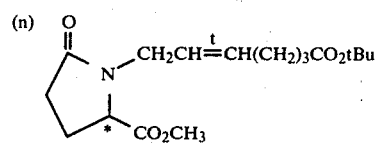
| Column E | Column F |
|---|---|
| (IV - d or l) | (V - d or l) |
(a) 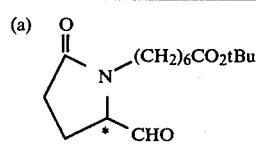
(a) 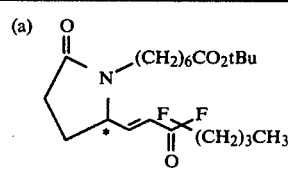
(b) 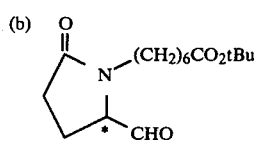
(b) 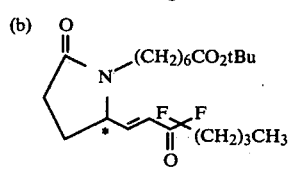
(c) 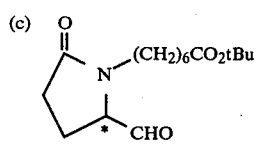
(c) 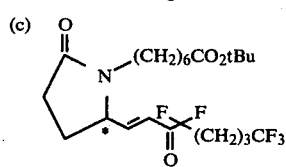
(d) 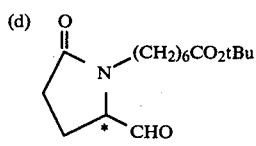
(d) 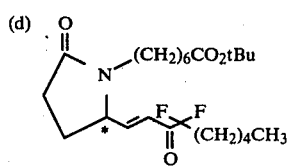
(e) 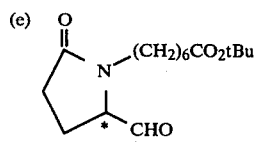
(e) 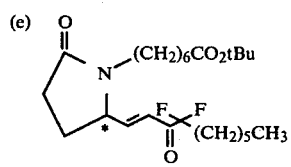
(f) 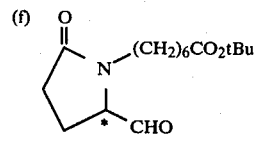
(f) 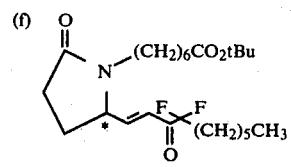
(g) 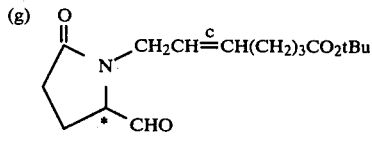
(g) 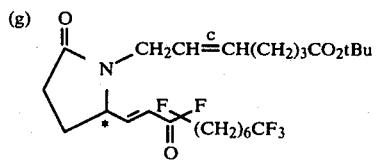
(h) 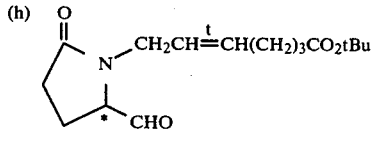
(h) 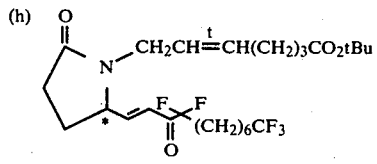
(i) 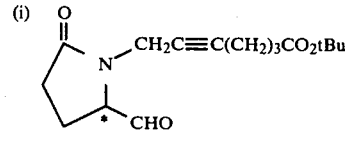
(i) 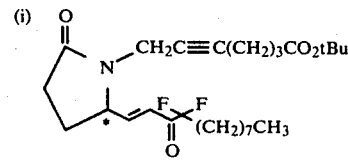

-continued
(j) 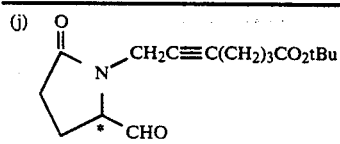
(j) 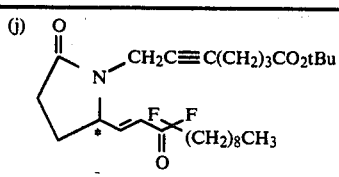
(k) 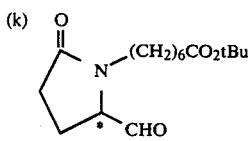
(k) 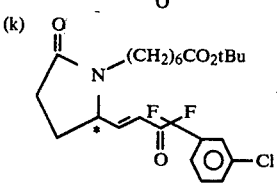
(l9) 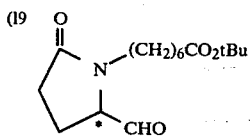
(l) 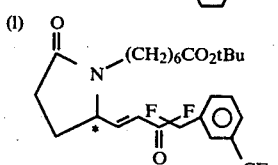
(m) 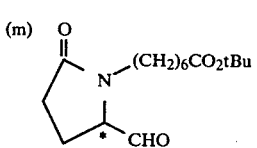
(m) 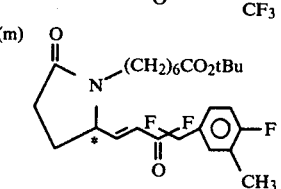
(n) 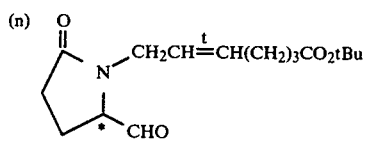
(n) 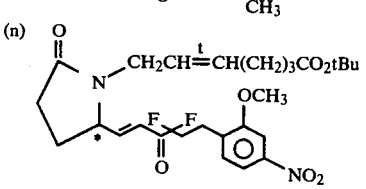
| Column G (IX - d or l) | Column H (R'MgX) |
|---|---|
| (a) 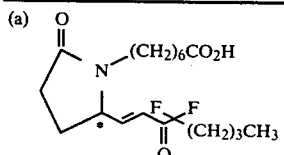 | (a) $CH_3MgCl$ |
| (b) — | (b) — |
| (c) 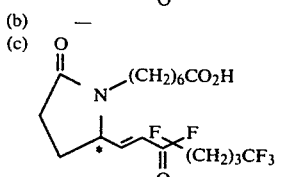 | (c) $C_2H_5MgBr$ |
| (d) — | (d) — |
| (e) — | (e) — |
| (f) 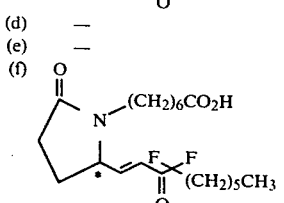 | (f) $CH_3MgI$ |
| (g) — | (g) — |
| (h) 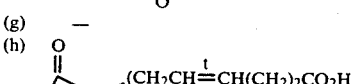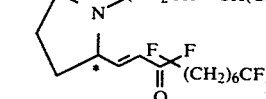 | (h) $C_2H_5MgCl$ |
| (i) — | (i) — |
| (j) — | (j) — |
| (k) — | (k) — |
| (l) — | (l) — |
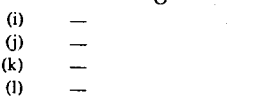

-continued
| | | | |
|---|---|---|---|
| (m) | 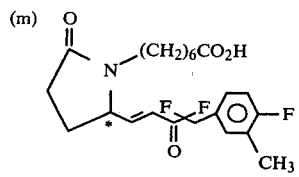 | (m) | CH₃MgBr |
| (n) | 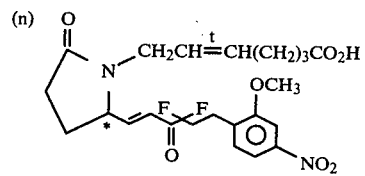 | (n) | CH₃MgBr |
| Column I (VI) | | Column J (VII - d or l) | |
|---|---|---|---|
| (a) | — | (a) | — |
| (b) | 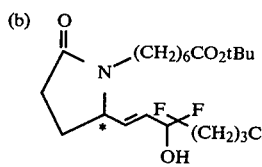 | (b) | 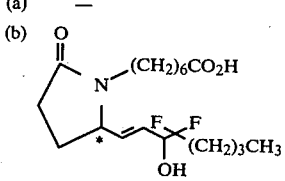 |
| (c) | — | (c) | — |
| (d) | 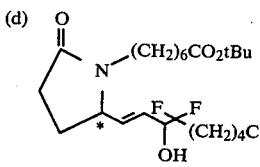 | (d) | 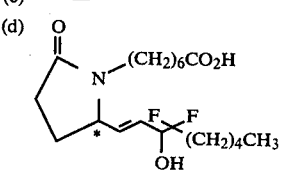 |
| (e) | 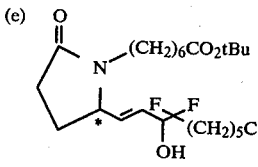 | (e) | 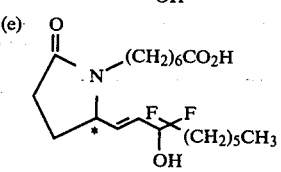 |
| (f) | — | (f) | — |
| (g) | 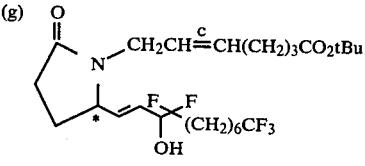 | (g) | 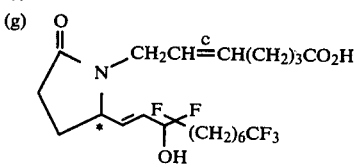 |
| (h) | — | (h) | — |
| (i) | 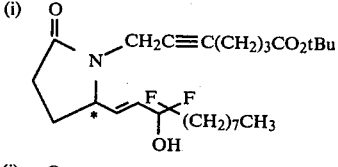 | (i) | 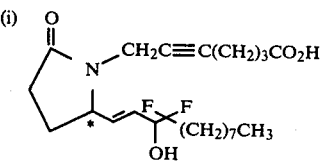 |
| (j) | 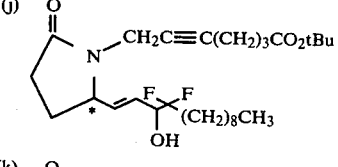 | (j) | 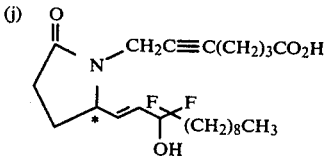 |
| (k) | 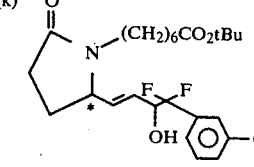 | (k) | 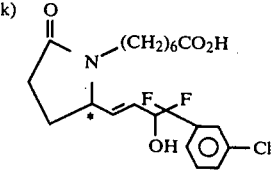 |

-continued
(l) 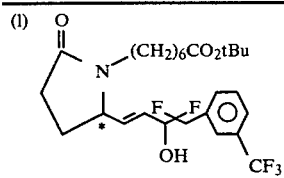 (l) 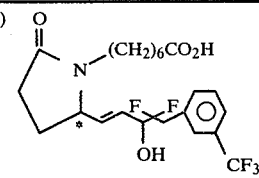
(m) — (m) —
(n) — (n) —
Column K
(VII-d or l, or X-d or l)
(a) 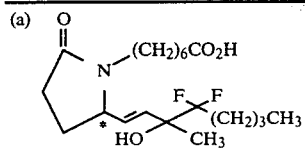 (j) 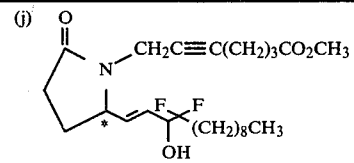
(b) 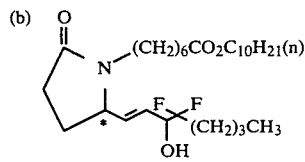 (k) 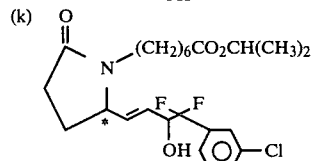
(c) 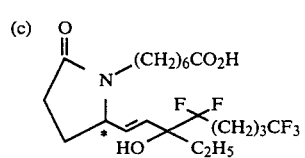 (l) 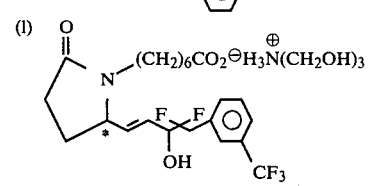
(d) 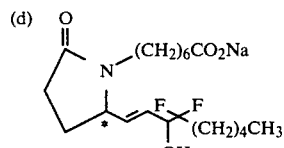 (m) 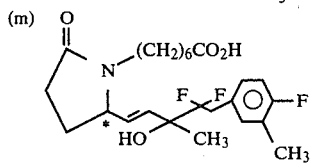
(e) 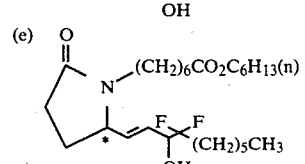 (n) 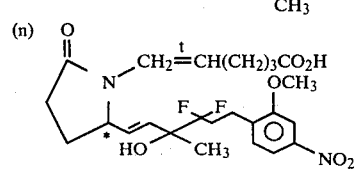
(f) 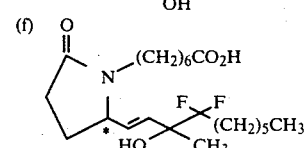
(g) 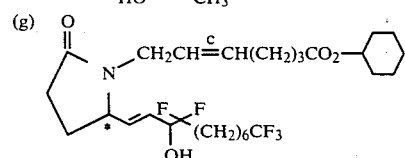
(h) 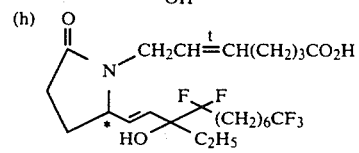
(i) 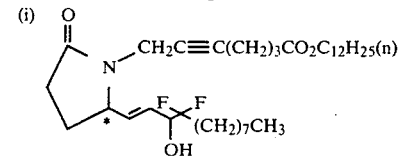
Column L -continued (XI - d or l)

| | |
|---|---|
| (a) 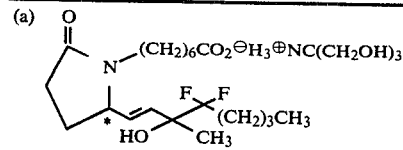 | (k) — |
| | (l) — |
| (b) — | (m) 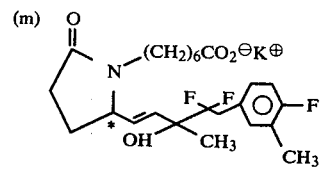 |
| (c) 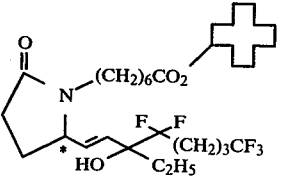 | (n) 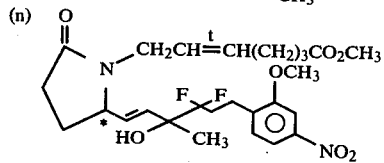 |
| (d) — | |
| (e) — | |
| (f) ![structure] N-(CH2)6CO2—⟨  F\\(CH2)5CH3  HO* CH3 | |
| (g) — | |
| (h) ![structure] N-CH2CH=CH(CH2)3CO2Ca/2  F\\(CH2)6CF3  HO* C2H5 | |
| (i) — | |
| (j) — | |

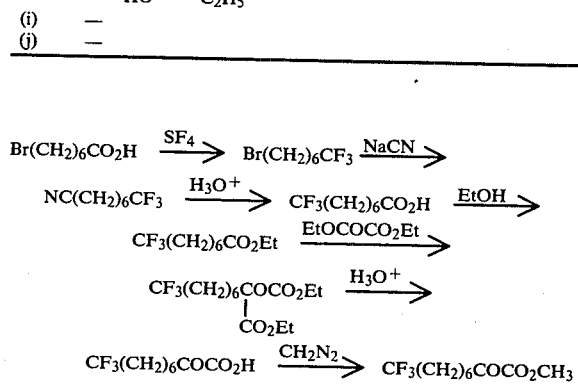

Conversion of the compounds of type II (Column B) to phosphonate III (Column C), the synthesis of esters XVI - d or l (Column D) and their reduction to aldehydes of type IV - d or l (Column E), and the reaction of phosphonate esters III with aldehydes IV - d or l to give ketones V - d or l (Column F), etc., are described in general above and in particular by the Examples.

UTILITY

The 8-aza-16,16-difluoroprostanoids of this invention are gastro-intestinal cytoprotective agents, inhibitors of histamine-induced bronchoconstriction or stimulators of smooth muscle or prostaglandin antagonists in experimental animals. Gastro-intestinal cytoprotective agents are of value as potential drugs, for example, for treatment or prevention of gastrointestinal inflammatory conditions. Inhibitors of histamine-induced bronchoconstriction are useful as potential anti-asthma agents.

Compounds of this invention, described, named, or depicted in their acid form should be understood to include the corresponding salts all of which would be expected by one skilled in the art to have similar activity.

The attractiveness of these compounds for drug use is enhanced because they are effective when taken orally as well as by injection or by inhalation. Furthermore, unlike natural prostaglandins of the PGE type, the compounds are quite stable chemically; for example, they would have a long shelf-life and are stable in moderately strong acid or basic media. Finally, the compounds of this invention are inexpensive and easy to make relative to the natural prostaglandins and many of their derivatives.

The optically-active 8-aza-16,16-difluoroprostanoids described in this invention are also useful as prostaglandin antagonists or as inhibitors of histamine-induced bronchoconstriction or as gastrointestinal cytoprotective agents. The latter effect is believed to arise because these compounds protect the mucosa of the stomach and intestine. This cytoprotective property indicates the value of these prostanoids in preventing or treating in humans or animal subjects peptic ulcer, such as gastric or duodenal ulcer, and inflammatory bowel disease such as colitis.

The advantage of having available different optical forms of these 8-aza-16,16-difluoroprostanoids lies in differences in the kind of biological activity exhibited by the different forms. For example, some of the optical forms are even more potent as cytoprotective agents in experimental animals than the racemic or optically-inactive forms. But some of the optical isomers which have relatively low potencies in cytoprotective tests exhibit greater potency as prostaglandin antagonists. Such compounds can inhibit certain biological effects ordinarily brought about by the natural prostaglandins, e.g., $PGE_1$, and by virtue of this property they are potentially useful as reagents for biochemical research, or as medical diagnostic agents, or as anti-diarrheal agents.

Some differences in the cytoprotective properties of these optical isomers are indicated by data in Table I. Using a method similar to that of Robert [U.S. Pat. No. 4,097,603 (1978)], fasted, male rats were treated with 8-azaprostanoids orally and various times later they were treated orally with 1.0 ml of absolute ethanol. The rats were sacrificed after ethanol administration and the stomachs were removed, inspected, and rated. The $ED_{50}$ values in Table I represent the doses of 8-aza-16,16-difluoroprostanoids that gave 50% protection from the necrosis and inflammation of the stomach caused by ethanol. Values for the natural prostaglandin $E_1$ ($PGE_1$) and for two known nonfluorinated 8-azaprostanoids are given for comparison.

TABLE I

| Compound No. | Ex. No. | Percent Protection 2 mg/kg, 1 hr* | $ED_{50}$ mg/kg at peak time | Peak Time** |
|---|---|---|---|---|
| 6 | 37 | 32 | | |
| 7 | 38 | 91 | .0035 | 15 min |
| 8 | 39 | 91 | .005 | 15 min |
| 13 | 40 | 66 | 0.8 | 15 min |
| 14 | 41 | — | 0.22 | 1 hr |
| 15 | 42 | 88 | 0.025 | 15 min |
| 6l (15RS) | 43 | 59 | | |
| 6d (15RS) | 43 | −5 | | |
| 6l (15R) | 44 | 59 | | |
| 6l (15S) | 44 | 9 | | |
| 7l (15R) | 45 | | .0007 | 15 min |
| 7l (15S) | 45 | | .010 | |
| 21 | 47 | 68 | | |
| 22 | 48 | 82 | | |
| $PGE_1$ | — | — | .011 | 5 min |
| 7-[2-oxo-5-(3-hydroxy-1-oct-1-enyl)-1-pyrrolidinyl]heptanoic acids | — | 40 | 3.0 | 1 hr |
| methyl 7-[2-oxo-5-(3-hydroxy-1-oct-1-enyl)-1-pyrrolidinyl]heptanoate | — | 60 | 1.8 | 1 hr |

*"1 hr" refers to the one hour interval between administration of compound and subsequent ethanol administration.
**"Peak Time" refers to that interval between administration of compound and administration of ethanol at which greatest protection is observed.

As has been mentioned, compounds of this invention also show activity as potential drugs for controlling bronchial asthma. Using an aerosol histamine challenge test in guinea pigs [a modification of the method of M. E. Rosenthale et al, *Experientia*, 26, 119 (1970)], the ability of 8-aza-16,16-difluoroprostanoids administered by i.p. injection to protect against histamine-induced bronchoconstriction was measured. Using injections of 0.5 mg/kg and evaluating the guinea pigs 60 minutes after the injections, compound 6 gave 40% protection, compound 6l (15 RS) gave 39% protection, and compound 6d(15 RS) gave 14% protection. An oral dose of compound 8 at 5 mg/kg gave 80% protection at 2 hours.

Certain compounds of this invention have been shown also to prevent indomethacin-induced ulcers in the small intestines of rats. This suggests that these compounds would be useful in preventing the ulcerogenic side-effects commonly associated with non-steroidal anti-inflammatory agents.

Certain compounds of this invention (including some which may not be the strongest cytoprotective agents) are the most potent as antagonists of the natural prostaglandin $PGE_1$. For example, optically active compound 6d(15 RS) which showed no (or a negative) cytoprotective effect (Table I) had an $IC_{50}$ of about 3–5 μg/ml against $PGE_1$, whereas the racemic compound 6 which showed some cytoprotective activity (Table I) was a weaker $PGE_1$ antagonist with an $IC_{50}$ of about 10 to 15 μg/ml. These $PGE_1$ antagonist tests were run on isolated rat stomach strips.

As pharmaceutical compositions useful for treating animal or human subjects, the 8-aza-16,16-difluoroprostanoids of this invention can be formulated as tablets or in capsules for oral administration, or in oils for administration by injection.

For example, a compressed tablet could be made by standard formulation techniques to contain the following ingredients (in mg per tablet):

| | |
|---|---|
| 8-azaprostanoid 7l (15 R) | 0.05 mg |
| corn starch | 24.95 mg |
| dicalcium phosphate . $2H_2O$ | 174.0 mg |
| magnesium stearate | 1.0 mg |
| total | 200.0 mg |

Or two-piece, hard-shelled gelatin capsules could be prepared by standard formulation techniques to contain the following ingredients (mg/capsule):

| | |
|---|---|
| 8-azaprostanoid 7l (15 R) | 0.10 mg |
| corn starch | 70.0 mg |
| dicalcium phosphate . $2H_2O$ | 249.9 mg |
| FD&C Yellow #5 - Aluminum Lake 25% | 2.0 mg |
| hydrogenated cotton seed oil | 25.0 mg |
| calcium stearate | 3.0 mg |
| total | 350.0 mg |

In dealing with minute quantities of these very potent 8-aza-16,16-difluoroazaprostanoids, it can be convenient to pre-absorb the compound on food-grade silica gel so that the silica gel contains about 1 to 20% by weight of active ingredient. Thus, absorption of 10% by weight of an azaprostanoid on 9μ Syloid ® silica gel gives a free-flowing powder that is easier to handle than some of the oily azaprostanoids and this free-flowing powder can then be mixed into tablet or capsule formulations such as those described above.

Injectable formulations of the compounds of this invention are made by dissolving the compounds in suitable inert media, e.g., in peanut oil or cotton seed oil, and sterilizing the solutions. An advantage of the compounds of this invention over natural prostaglandins of the PGE type, and over many of their synthetic analogs, is their greater chemical and thermal stability, which permits sterilization of their solutions by brief heating in sealed ampules.

Oral and injectable formulations of the compounds of this invention are contemplated for utility in the treatment or prevention of gastrointestinal diseases, such as gastric ulcers, duodenal ulcers, or colitis. They should also be useful for the control of bronchial asthma. Aerosol formulations of these compounds also could be used for the latter. For example, a typical formulation would be a suspension or solution of an 8-aza-16,16-difluoroprostanoid, in a mixture of trichloromonofluoromethane and dichlorodifluoromethane with a small amount of oleic acid, which can be aerosolized for oral inhalation.

EXAMPLES

The following Examples illustrate the invention.

In accord with convention, wavey lines, representing bonds between carbon and OH, mean that a mixture of the two possible absolute configurations is present. Wedge shaped bonds represent bonds protruding out of the plane of the paper. Bonds represented by broken lines represent bonds extending behind the plane of the paper. As already pointed out, asterisks designate chiral carbon atoms in one or predominantly one of two possible absolute configurations.

Examples 1 to 36

The compounds described in Columns I, J, K and L prepared according to the general reaction sequence depicted above are Examples of this invention according to the following key:

| Example No. | Compound Column and Letter | Example No. | Compound Column and Letter |
| --- | --- | --- | --- |
| 1 | Ib | 19 | Kc |
| 2 | Id | 20 | Kd |
| 3 | Ie | 21 | Ke |
| 4 | Ig | 22 | Kf |
| 5 | Ii | 23 | Kg |
| 6 | Ij | 24 | Kh |
| 7 | Ik | 25 | Ki |
| 8 | Il | 26 | Kj |
| 9 | Jb | 27 | Kk |
| 10 | Jd | 28 | Kl |
| 11 | Je | 29 | Km |
| 12 | Jg | 30 | Kn |
| 13 | Ji | 31 | La |
| 14 | Jj | 32 | Lc |
| 15 | Jk | 33 | Lf |
| 16 | Jl | 34 | Lh |
| 17 | Ka | 35 | Lm |
| 18 | Kb | 36 | Ln |

EXAMPLE 37 racemic tert-Butyl 7-[2-Oxo-5(RS)-5-(4,4-difluoro-3(RS)-3-hydroxy-1n-dec-1(E)-enyl)-1-pyrrolidinyl]-heptanoate (6)

a. Methyl 2,2-Difluorooctanoate (2)

Methyl 2-oxooctanoate (10.7 g, 0.62 mole) was stirred with cooling in an ice bath while 16 g (0.100 mole) of diethylaminosulfur trifluoride (DAST) [Middleton, *J. Org. Chem.*, 40, 574 (1975); U.S. Pat. No. 3,976,691 (1976)] was added dropwise. The mixture was stirred for 24 hrs letting the ice melt slowly, and then poured into 300 cc of ice water. The aqueous mixture was extracted with ether, the ether was washed twice with 5% HCl and twice with saturated NaCl. Drying over CaSO$_4$, evaporation of the ether, and distillation of the mobile liquid at about 40°/4 mm gave B 9.8 g (81%) of the fluoroester 2; HRMS calcd for C$_9$H$_{16}$F$_2$O$_2$ 194.1117, measured 194.1120, $^{19}$F nmr (CDCl$_3$, F-11) triplet at −106.26 ppm, proton decoupled to singlet; pmr (CDCl$_3$—TMS) 3.88 ppm (s, OCH$_3$, 3), etc. Another sample of 2 prepared similarly was distilled at 75°/10 mm.

b. Dimethyl 3,3-Difluoro-2-oxo-n-nonylphosphonate (3)

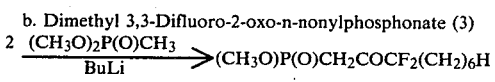

Under nitrogen, a solution of 6.2 g (50.0 mmoles) of dimethyl methylphosphonate in 100 ml of tetrahydrofuran (THF) was cooled to about −78° and 26.0 ml of 1.6 M (41.6 mmoles) of butyl lithium was added dropwise over about 15 min. The mixture was stirred for 40 min and, with continued cooling, a solution of 4.0 g (20.6 mmoles) of difluoroester 2 in 10 ml of THF was added dropwise over 7 min. The cold mixture was stirred for 10 min (only) and poured directly into 500 cc of saturated aqueous NH$_4$Cl and extracted twice with ether. The ester solution was washed once with saturated NaCl solution, dried over MgSO$_4$/CaSO$_4$, and evaporated, giving 6.0 g of the crude phosphonate ester. Bulb-to-bulb distillation gave 5.0 g (85%) of 3 at 136° to 138°/12 to 22μ, as a colorless, mobile liquid; $^{19}$F nmr (CDCl$_3$, F-11), −106.61 ppm as a singlet when proton-decoupled, and a triplet when proton coupled; pmr (CDCl$_3$-TMS) 3.2 (d, 2, J=22 Hz, COCH$_2$P), 3.7 (d, 6, J=11 Hz, CH$_3$O); HRMS (direct inlet 100°) calcd. m/e for M+ of C$_{11}$H$_{21}$O$_4$F$_2$P 286.1144, meas. 286.1146; m/e for M−CF$_2$(CH$_2$)$_6$H 151.0160, meas. 151.0161.

c. racemic tert-Butyl 7-[2-Oxo-5-(RS)-5-(4,4-difluoro-3-oxo-1-n-dec-1(E)-enyl)-1-pyrrolidinyl]heptanoate (5)

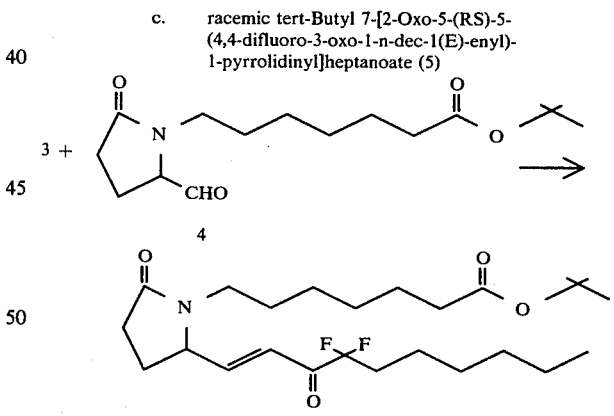

In a dry flask under nitrogen, 0.540 g of 55% sodium hydride (0.297 g, 12.4 mmoles) was washed with petroleum ether to remove the oil and then 40 ml of dry ethylene glycol dimethyl ether (glyme) was added. The mixture was cooled in an ice bath and stirred while a solution of 4.25 g (14.8 mmoles) of the phosphonate ester 3 in 50 ml of glyme was added dropwise over 25 min. The mixture was stirred for 5 min more with cooling, by which time it was clear of suspended material. A solution of 3.9 g (13.13 mmoles) of tert-butyl 7-[2-oxo-5(RS)-formyl-1-pyrrolidinyl]heptanoate (4) in 12 ml of glyme was added all at once; the mixture was stirred at room temperature for 1.5 hrs and then heated at reflux temperature for 2 hrs. The mixture was cooled, concentrated under reduced pressure, and partitioned between water and ether. The ether was washed successively with $H_2O$, 5% $NaHCO_3$, and saturated NaCl, dried over $MgSO_4/CaSO_4$, and evaporated, giving 6.4 g of amber oil, the crude difluoro ketone 5. TLC (silica gel, EtOAc) indicated that it was about 90% pure. Purification by HPLC (2:1 ethyl acetate/hexane) gave 3.67 g of 5 as a light yellow oil; $^{19}F$ nmr ($CDCl_3$, F-11) $-107.47$ ppm (proton coupled triplet, proton decoupled singlet); pmr ($CDCl_3$, TMS) vinyl protons at 6.4 to 7.1 ppm as AB pattern centered at 6.7 ppm and the lower field set of doublets split further (J=18 Hz) by N-C$\underline{H}$-CH=; TLC indicated 100% purity ($R_f$=0.45, silica gel; 2:1 ethyl acetate/hexane).

d. racemic tert-Butyl 7-[2-Oxo-5(RS)-5-(4,4-difluoro-3(RS)-hydroxy-1n-dec-1(E)-enyl)-1-pyrrolidinyl]heptanoate (6)

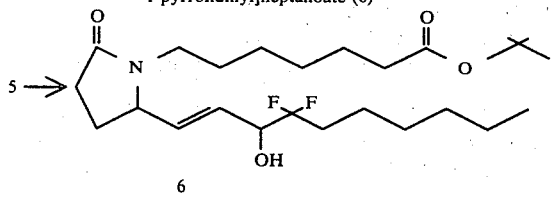

A solution of 2.8 g (6.1 mmoles of the pure ketone 5 in 80 ml of ethanol was cooled to $-20°$ under nitrogen and 0.50 g (12.2 mmoles) of $NaBH_4$ was added. The mixture was stirred at $-20°$ for 0.5 hr, kept in a freezer at about $-20°$ for an additional 1.7 hrs, and then poured into 500 ml of saturated $NH_4Cl$ solution. This was extracted with ethyl acetate twice and the ethyl acetate extract was washed with saturated NaCl once, dried over $MgSO_4/CaSO_4$, and evaporated, giving 3.0 g of 6 as a mixture of 4 optical isomers (2 diastereomeric sets of enantiomers); TLC (EtOAc, silica gel) 2 spots, RF. ca. 0.5.

EXAMPLE 38 racemic 7-[2-Oxo-5(RS)-(4,4-difluoro-3(RS)-hydroxy-1-n-dec-1(E)-enyl)-1-pyrrolidinyl]heptanoic Acid (7)

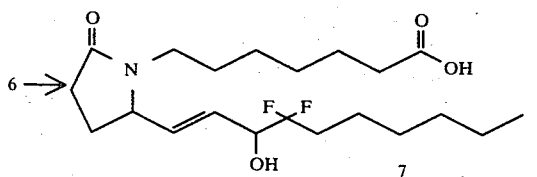

Ester 6 (2.4 g) was cooled in an ice bath while 200 ml of 85% $H_3PO_4$ was added to the flask all at once with stirring. After 5 min the mixture was stirred with no cooling for 4 hrs and then poured into 200 cc of ice water. NaCl (10 g) was added and the mixture extracted twice with ethyl acetate, which was washed twice with saturated aqueous NaCl. Evaporation of the ethyl acetate gave 3 g of an oil that was dissolved in about 100 ml of 5% $NaHCO_3$; the aqueous solution was filtered through paper and the clear filtrate acidified with excess conc. HCl. Extraction with ethyl acetate twice, drying, and evaporation gave 2.06 g (98%) of the acid 7 as an oil; $^{19}F$ nmr ($CDCl_3$, F-11) (proton decoupled) showed two sets (2 diastereomers) of AB patterns, with 2 peaks centered at $-107.30$, two centered at $-109.95$, one peak (or 2 "superimposed" peaks) at $-111.30$, and one peak (or 2 "superimposed" peaks at $-113.95$ ppm); (at some concentrations the "superimposed" peaks were discernable as separate peaks); pmr vinyl portons (2) at 5.7 ppm, etc.; HRMS (for another sample prepared similarly calculated for $C_{21}H_{35}F_2NO_4$ m/e for $M^+$ 403.2532, measured 403.2520; calculated for M-$C_8H_{15}F_2O$ 238.1442, measured 238.1443. Like ester 6, acid 7 was a mixture of four optical isomers in approximately equal amounts.

EXAMPLE 39 racemic Methyl 7-[2-Oxo-5(RS)-5-(4,4-difluoro-3(RS)-3-hydroxy-1-n-dec-1-(E)-enyl)-1-pyrrolidinyl]heptanoate (8)

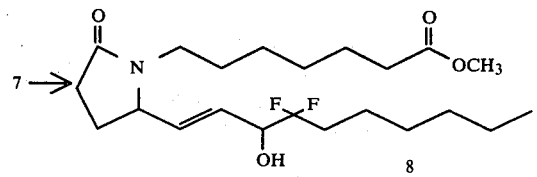

Acid 7 (1.2 g) in ether was treated with a slight excess of diazomethane and then with a little acetic acid to decompose the diazomethane. The ether solution was washed with 5% $NaHCO_3$, dried, and evaporated. Purification of methyl ester 8 by HPLC (ethyl acetate) gave 1.06 g of ester 8 as a colorless oil that, according to TLC on silica gel (EtOAc, Rf=0.4), was quite pure; HRMS on another sample prepared similarly, calculated for $C_{22}H_{37}F_2NO_4$, 417.2688, measured 417.2675; M—$H_2O$ calculated 399.2583, measured 399.2589; M—$CH_3O$ calculated 386.2505, measured 386.2506; M—$CH_2CO_2CH_3$ calculated 344.2399, measured 344.2397; M—$(CH_2)_5CO_2CH_3$ calculated 288.1774, measured 288.1775; M—$CH(OH)CF_2(CH_2)_6H$ calculated 252.1610, measured 252.1598.

EXAMPLE 40 racemic t-Butyl 7-[2-Oxo-5(RS)-5-(4,4-difluoro-3(RS)-3-hydroxy-1-n-oct-1(E)-enyl)-1-pyrrolidinyl]heptanoate (13)

a. Methyl 2,2-Difluorohexanoate (10)

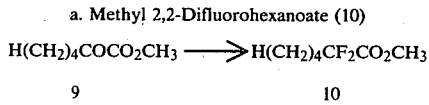

The 2-oxocaproic acid was prepared by the method of Adickes et al [*Ann.*, 555, 41 (1944)] and converted to the methyl ester 9 by diazomethane.

A solution of 19.0 g (0.106 mole) of ester 9 in 40 ml of $CH_2Cl_2$ was cooled in an ice bath and 20 ml (26 g, 0.164 mole) of diethylaminosulfur trifluoride was added dropwise. The mixture was stirred at room temperature for about 18 hrs, poured into ice, and the $CH_2Cl_2$ separated, washed once with 5% HCl, dried, and evaporated under aspirator vacuum. Distillation of the remaining liquid through a Vigreux column gave 18.39 g (92%) of the difluoroester 10 as a colorless liquid bp 60°/20 mm; $^{19}F$ ($CDCl_3$, F-11) singlet $-106.24$ ppm (proton decoupled), or triplet (J=17 Hz) (proton coupled); pmr ($CDCl_3$, TMS) 2 ppm (multiplet, $CH_2CF_2$), no $CH_2CO$ at 2.75 ppm.

b. Dimethyl 3,3-Difluoro-2-oxo-n-heptylphosphonate (11)

A solution of 24.8 g (0.2 mole) of dimethyl methylphosphonate in 400 ml of dry THF was cooled in a dry ice acetone bath and 104 ml of 1.6 M (0.166 mole) butyl lithium/hexane was added dropwise over about 45 min, keeping the temperature less than −70°. The mixture was stirred at about −78° for 30 min more and then 13.7 g (0.0825 mole) of fluoroester 10 in 20 ml of THF was added dropwise over a period of 15 min; the temperature of the reaction mixture was kept at less than −71°. The mixture was stirred at −71° to −76° for only 10 min more and then poured directly into 1 l of saturated NH4Cl solution. Then 25 ml of concentrated HCl was added to the aqueous mixture, which was extracted twice with ether. The organic layer was washed once with saturated NaCl, dried over MgSO4/CaSO4, and evaporated, giving an oil and a white solid. The oil and solid were taken up in toluene and the solution reevaporated at 55° under vacuum. The remaining clear oil was distilled bulb-to-bulb at 110° to 115°/10–20μ, giving 19.88 g (93%) of phosphonate ester 11 as a colorless, mobile liquid; pmr (CDCl3, TMS) 3.25 ppm (d, J=22 Hz, PCH2CO, 2) 3.7 ppm (d, J=12 Hz, CH3O, 6); HRMS calculated for m/e for M+ of $C_{19}H_{17}O_4F_2P$: 258.0831, measured 258.0840; calculated for M-HF 238.0764, measured 238.0769; calculated for M—$C_5H_9F_2$ 151.0168, measured 151.0160.

c. racemic tert-Butyl 7-[2-Oxo-5(RS)-5-(4,4-difluoro-3-oxo-1-n-oct-1(E)-enyl)-1-pyrrolidinyl]heptanoate (12)

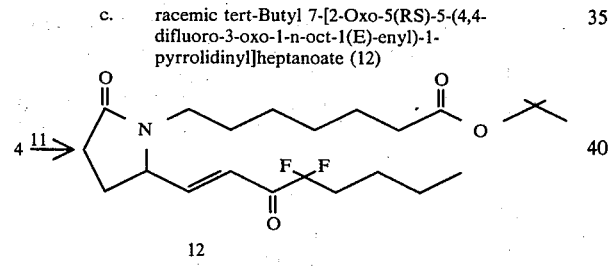

In a dry flask under nitrogen, 1.04 g of 55% sodium hydride in oil (0.572 g NaH, 23.8 mmoles) was washed with petroleum ether and then 70 ml of glyme was added. The mixture was cooled in an ice bath and stirred while a solution of 6.45 g (25 mmoles) of phosphonate ester 11 in 50 ml of glyme was added dropwise over 25 min. The mixture was stirred for 5 min with cooling and then to the clear solution 8.6 g (28 mmoles) of tert-butyl 7-(2-oxo-5(RS)-formyl-1-pyrrolidinyl)heptanoate (4) in 20 ml of glyme was added all at once. The mixture was stirred at room temperature for 2 hrs and then heated at reflux temperature for 2 hrs. The mixture was cooled, concentrated under reduced pressure and partitioned between water and ether. The ether was washed successively with water, 5% NaHCO3, saturated NaCl, dried over MgSO4/CaSO4, and evaporated giving 10.9 g of difluoro ketone 12 as an amber oil. TLC (silica gel, ethyl acetate) indicated that it was about 90% pure (Rf=0.5).

d. racemic tert-Butyl 7-[2-Oxo-5(RS)-5-(4,4-difluoro-3(RS)-3-hydroxy-1n-oct-1(E)-enyl)-1-pyrrolidinyl]heptanoate (13)

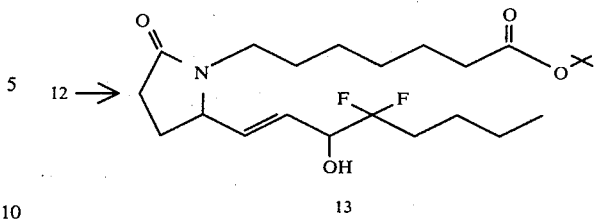

To a solution of 8.0 g (18.6 mmoles) of ketone 12 in 100 ml of ethanol at −20° under nitrogen was added 1.5 g (37 mmoles) of NaBH4. The mixture was stirred at −20° for 0.5 hrs and then kept in a freezer at about −20° for 1.25 hr. The cold mixture was poured into 600 ml of saturated NH4Cl solution and extracted three times with ethyl acetate. The ethyl acetate was washed with saturated NH4Cl, dried, and evaporated, giving 8.46 g of 13 as an oil that according to TLC (silica gel, EtOH) was about 95% pure (Rf=0.6). Purification by HPLC on silica gel (EtOAc) gave 4.81 of pure 13 as an oil; HRMS calculated for $C_{23}H_{39}NO_4F_2$: 431.2845, measured 431.2813; calculated for M—H2O: 413.2729, measured 413.2776; calculated for M—C4H9: 374.2141, measured 374.2127.

EXAMPLE 41 racemic 7-[2-Oxo-5(RS)-5-(4,4-difluoro-3(RS)-3-hydroxyl-1-n-oct-1(E)-enyl)-1-pyrrolidinyl]heptanoic Acid (14)

A solution of 4.6 g of ester 13 in 5 ml of tetrahydrofuran was added with stirring to 46 ml of 85% H3PO4 that was cooled in an ice bath. The ice bath was removed and the mixture was stirred for 4 hrs. It was then poured into 400 ml of water containing about 30 g of NaCl. Extraction with three 75 ml portions of methylene chloride, washing the methylene chloride extract with saturated aqueous NaCl, and evaporation of the solvent, gave about 5 g of an oil. This oil was dissolved in about 40 ml of 5% NaHCO3 and the solution washed once with ether. The aqueous solution was then acidified with concentrated HCl and extracted with ethyl acetate. The ethyl acetate was dried and evaporated, giving 4.0 g (100%) of the acid 14; TLC (EtOAc/2% AcOH, silica gel) Rf=ca. 0.26; 19F nmr (CDCl3, F-11): 2 AB patterns, with chemical shifts close to those observed for compound 7; HRMS calculated for $C_{19}H_{31}F_2NO_4$: 375.2219, measured 375.2184; calculated for M—H2O: 357.2114, measured 357.2142; calculated for M—(CH2)3CO2H: 288.1774, measured 288.1761; calculated for M—$C_6H_{11}F_2O$: 238.1442, measured 238.1446.

Compound 14 is a preferred compound of this invention; both in its racemic form and optically-active forms. An optically-active form prepared in a manner analogous to the preparation of the optically-active compound 7I(15 R) (Example 45) would be named 7-[2- oxo-5(R)-5(4,4-difluoro-3(R)-3-hydroxy-1-n-oct-1(E)-enyl)-1-pyrrolidinyl]heptanoic acid

EXAMPLE 42 a. racemic Methyl 7-[2-Oxo-5(RS)-5-(4,4-difluoro-3(RS)-3-hydroxy-n-oct-1(E)-enyl)-1-pyrrolidinyl]heptanoate (15)

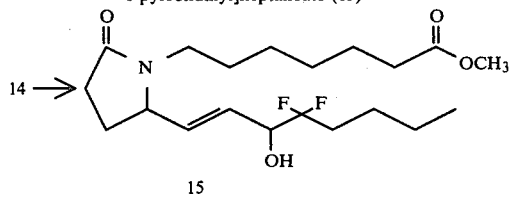

Acid 14 (1.5 g) was treated with a slight excess of diazomethane in ether, giving on evaporation of the ether, methyl ester 15; purification by HPLC (EtOAc) gave 1.39 g of 15 as a colorless oil. HRMS: calculated for $C_{20}H_{33}F_2NO_4$: 389.2376, measured 389.2379; calculated for M—$(CH_2)_5CO_2CH_3$: 260.1461, measured 260.1470; calculated for M—$C_6H_{11}F_2O$: 252.1598, measured 252.1576.

EXAMPLE 43 d(+) and l(−) tert-Butyl 7-[2-Oxo-5(R or S)5(4,4-difluoro-3-hydroxy-1n-dec-1(E)-enyl)-1-pyrrolidinyl]heptanoate a. rac tert-Butyl 7-(2-Oxo-5-carboxy-1-pyrrolidinyl)heptanoate (17)

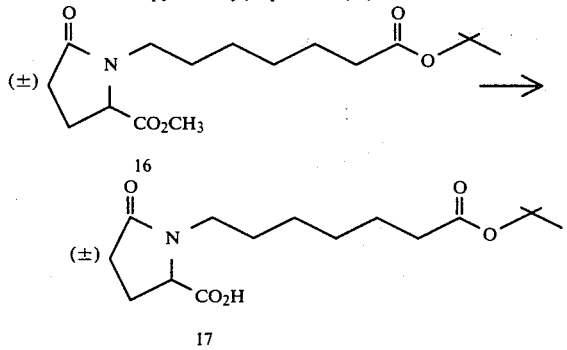

Racemic tert-butyl 7-(2-oxo-5-methoxycarbonyl-1-pyrrolidinyl)heptanoate (32.7 g, 0.1 mole) which had been purified by distillation through a wiped-film molecular still, was dissolved in 60 ml of methanol and, with stirring and cooling so that the reaction mixture stayed at 15°±3°, 1.0 N NaOH was added dropwise. When 90 ml of the caustic had been added, 3 drops of a 1% phenolphthalein indicator solution was added and enough additional caustic was added until a slight pink color persisted for 10 min. A total of 93.5 ml of 1 N NaOH was thus used. The mixture was concentrated under vacuum, mixed with 200 ml of water, and the water solution washed twice with ether, which was discarded. The aqueous solution was cooled in an ice bath and treated with 110 ml of 1.0 N HCl dropwise. Extraction with ether, drying over MgSO4, and evaporation of the ether, gave 28 g (89%) of white crystalline racemic acid 17; mp 49° to 51°. For another sample prepared in the same way: analysis calculated for $C_{16}H_{27}NO_5$: C, 61.32; H, 8.68; N, 4.47; found: C, 60.86; H, 8.52; N, 4.80.

Similarly, 65.6 g of crude racemic diester 16 that had not been previously purified by distillation was saponified in 80 ml of methanol by slow addition of 1.0 N NaOH at 35° over 2 hrs. The racemic acid 17 was isolated similarly and amounted to 51 g, mp 48° to 50°. This represents a significant simplification of the process used for preparing acid 17 because it eliminates the need for molecular distillation of the crude diester 16.

b. α-Methylbenzylamine salts of rac acid 17 (18d, 18l)

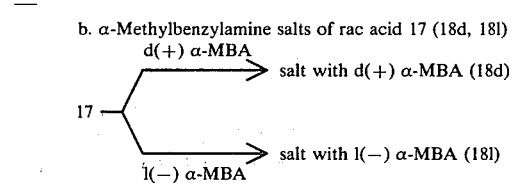

A solution of 66.37 g (0.212 mole) of rac acid 17 in 212 ml of ether was stirred with ice cooling and under nitrogen while 25.66 g (0.212 mole) of d(+)-α-methylbenzylamine diluted to 50 ml with ether was added quickly from a dropping funnel. The mixture was seeded with crystals of the d(+) amine salt (obtained earlier) and stirred at room temperature for about 23 hrs. The crystalline solid was collected under nitrogen (the wet salt is hygroscopic, the pure salt is not), affording 24.9 g of salt (18d). This salt was recrystallized from 50 ml of ethyl acetate giving 20.3 g of pure salt 18d; mp 100° to 102°.

The ethyl acetate and ether filtrates from above were combined, cooled in ice, and treated with 125 ml of 2 N HCl with stirring. The organic layer was separated, washed with two 75-ml portions of 1 N HCl, washed twice with saturated NaCl, and dried over Drierite ®. Evaporation of the solvent gave 51.96 g of acid 17 as an oil enriched in one enantiomer. This oil was dissolved in 200 ml of ether, and treated with 20.1 g of l(−)α-methylbenzylamine in 50 ml of ether at 0°. The mixture was seeded, kept at 0° for 1 hr, and filtered, giving 20.7 of the salt 18l, which was recrystallized from 40 ml of ethyl acetate to give 15.4 g of salt 18l; mp 100° to 103°.

The combined ether and ethyl acetate filtrates from precipitation of the salt 18l were treated with HCl as in the previous paragraph and the crude acid 17 obtained was retracted with one equivalent of d(+)α-methylbenzylamine, etc., as above, to give, in a total of three cycles, 30.4 g of recrystallized salt 18d. Two additional cycles gave a total of 25.4 g of recrystallized salt 18l.

Very pure samples of both salts, prepared similarly but recrystallized several times from ethyl acetate, had mp 101° to 103° (mixed mp 73° to 90°). For salt 18d: Analysis Calculated for $C_{24}H_{38}N_2O_5$: C 66.23; H 8.81; N 6.45; Found: C 66.40; H 8.74; N 6.40.

Specific rotation of salts 18d and 18l did not change significantly after two crystallizations from ethyl acetate (c=3.33, ethanol):

|  | 18d | 18l |
|---|---|---|
| $[\alpha]_D$ | −2.8° | +2.3 |
| $[\alpha]_{365}$ | −50.6° | +49.0 | c. d(+) tert-Butyl 7-(2-Oxo-5-carboxy-1-pyrrolidinyl)heptanoate (17d) and l(−) tert-Butyl 7-(2-Oxo-5-carboxy-1-pyrrolidinyl)heptanoate (17l)

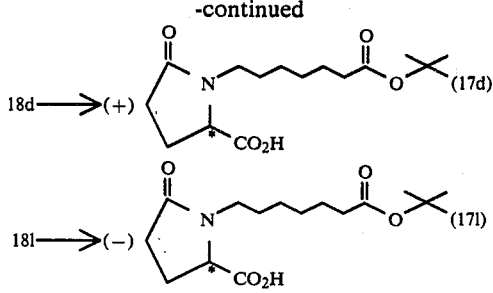

Treatment of 0.434 g of salt 18d with 50 ml of ether, 8 ml of water, and 2.0 ml of 1 N HCl gave in the ether layer after washing with 10 ml of 0.1 N HCl, and then washing with saturated NaCl and drying over MgSO$_4$, 0.303 g (97%) of the resolved acid 17d as a colorless liquid, $[\alpha]_D + 0.9°$ (EtOH). Similarly, salt 18l was converted to resolved acid 17l, $[\alpha]_D - 1.0°$ (EtOH).

Acid 17d is one, or predominantly one, enantiomer, believed to have the absolute configuration represented by 17(R), whereas acid 17l is one, or predominantly one, enantiomer believed to have an absolute configuration represented by 17(S).

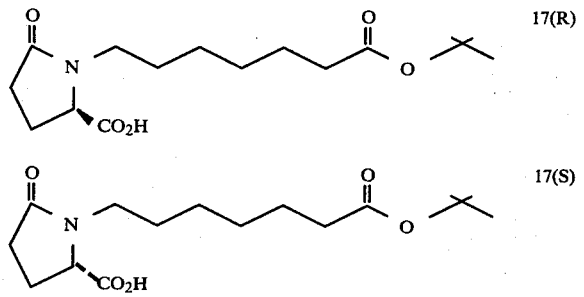

It is to be understood that the absolute configurations represented above by structures 17(R) and 17(S) and, subsequently, for compounds derived from these acids are based on signs of optical rotation, chromatographic behavior, and biological properties of interrelated members of the series of compounds.

d. d(+) tert-Butyl 7-(2-Oxo-5-methoxycarbonyl-1-pyrrolidinyl)heptanoate (16d) and l(−) tert-Butyl 7-(2-Oxo-5-methoxycarbonyl-1-pyrrolidinyl)heptanoate (16l)

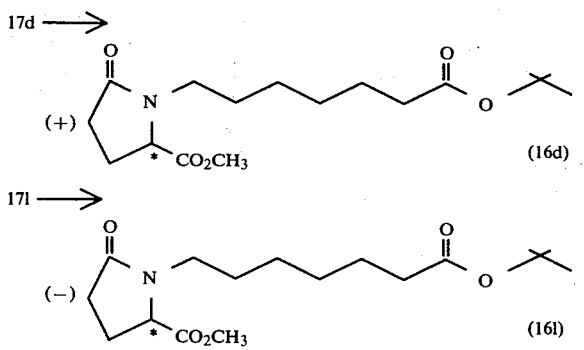

Treatment of resolved acid 17d (9.06 g) (prepared similarly to that described above) with excess diazomethane in ether, gave 8.53 g of the corresponding resolved methyl ester (16d); $[\alpha]_D + 6.2°$ (±0.1°), $[\alpha]_{365} - 31.4°$ (±0.1°) (C=6.67 EtOH).

Similarly, treatment of resolved acid 17l (9.4 g) (prepared in a manner similar to that described for 17l in the previous Example) with excess diazomethane in ether gave 8.68 g of ester 16l (EtOH); $[\alpha]_D - 6.3°$ (±0.1°), $[\alpha]_{365} + 31.5°$ (±0.1°) (C=6.67 EtOH).

e. d and l tert-butyl 7-(2-Oxo-5-formyl-1-pyrrolidinyl)heptanoate (4d and 4l)

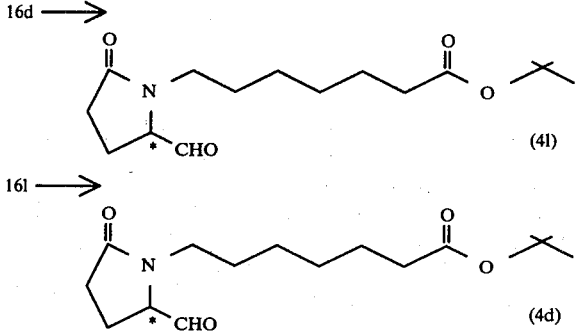

A solution of 3.27 g of resolved ester 16d in 15 ml of tetrahydrofuran (THF) was cooled to −78° and 2.5 ml of a 70% solution of sodium bis(2-methoxyethoxy) aluminum hydride in toluene (Vitride T ®) in 10 ml of THF was added dropwise with stirring. The mixture was stirred for 2.5 hrs with continued cooling, poured into about 300 ml of saturated oxalic acid solution, and extracted three times with ether. The ether was dried over CaSO$_4$ and evaporated giving 2.49 g (84%) of resolved aldehyde 4l as a colorless oil. The aldehyde was dried further, dehydrating the aldehydrol present, by dissolving it in toluene and removing the toluene under reduced pressure at about 50°.

Similarly, 4.9 g of resolved ester 16l in 20 ml of THF at −78° was treated with 3.8 ml of Vitride T ® solution in 15 ml of THF for 6 hrs, giving 3.91 g (71%) of resolved aldehyde 4d as a colorless oil; pmr (CDCl$_3$, TMS) 9.58 ppm (d, J=2.5 Hz CHO, 1) ppm, and other peaks identical to those observed for the racemic (d,l) tert-butyl 7-(2-Oxo-5-formyl-1-pyrrolidinyl)heptanoate (U.S. Pat. No. 3,975,399).

In another, modified procedure 7.1 g (22.6 mmoles) of ester 16l in 35 ml of THF at −78° was treated dropwise with a solution of 5.2 ml of Vitride T ® in 50 ml of THF. The addition was carried out very slowly over 1.25 hrs and then the reaction mixture was kept at −78° for 5 hrs before pouring into 400 ml of water containing 15 g of oxalic acid and saturated with respect to NaCl. After 3 extractions with ether, drying of the ether over MgSO$_4$ and CaSO$_4$, and evaporation of the ether, there was obtained the optically active aldehyde 4d. Aldehyde 4d was then dried by evaporation of its toluene solution as described above, giving 6.9 g of aldehyde 4d as a light yellow oil, $[\alpha]_{365} + 29.4°$ (c=3.33 ethanol).

Similarly, ester 16d was treated with Vitride T ® by this modified procedure giving aldehyde 4l as a light yellow oil, $[\alpha]_{365} - 24.8°$ (c=3.33 ethanol). Optically-active aldehyde 4l (derived from the d ester) is believed to be predominantly the enantiomer represented by 4(R) and optically-active aldehyde 4d (derived from the l ester) is believed to be predominantly the enantiomer represented by 4(S).

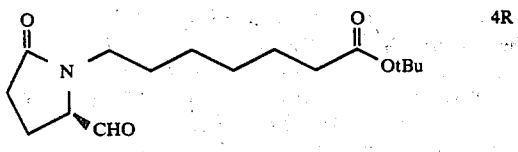
4R

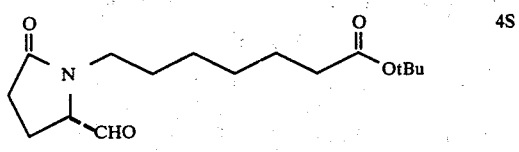
4S f. l and d tert-Butyl 7-[2-Oxo-5(R or S)5-(4,4-difluoro-3-oxo-1n-dec-1(E)-enyl)-1-pyrrolidinyl]heptanoate (5l and 5d)

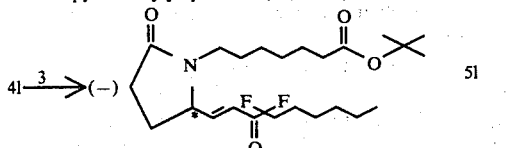
5l

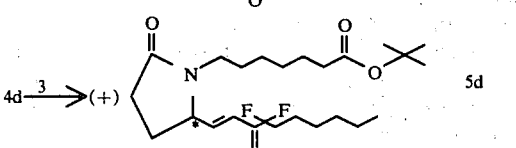
5d

A suspension of 12.4 mmoles of NaH in glyme was prepared by washing under nitrogen 0.540 g of 55% NaH/oil with petroleum ether and then adding 20 ml of glyme. With cooling in an ice bath and with stirring, a solution of 4.25 g (14.8 mmoles) of dimethyl 3,3-difluoro-2-oxo-n-nonylphosphate in 15 ml of glyme was added dropwise over about 15 min. The sodium salt was stirred at 0° for 5 min and then to the clear solution was added 4.1 g (13.8 mmoles) of aldehyde 4l in 15 ml of glyme. The reaction mixture was heated at reflux temperature for 1.5 hrs, cooled, and concentrated under reduced pressure at 40°. The residue was mixed with saturated NH4Cl solution and extracted with ether. The ether was dried (MgSO4/CaSO4) and incorporated, and the crude ketone 5l was purified by HPLC (EtOAc then 3:1 EtOAc/hexane). The pure, optically-active 8-azaprostanoid 5l thus obtained was a colorless oil weighing 2.77 g (49% yield); [α]$_D$ −0.5°; [α]$_{405}$ −20.7° (c=3.33, dioxane); HRMS calculated for C$_{21}$H$_{33}$O$_4$NF$_2$ (m/e of M—C$_4$H$_9$): 401.2376, measured 401.2401.

A suspension of 19.6 mmoles of NaH in 60 ml of glyme was prepared similarly from 0.867 g of 55% NaH/oil. This was kept at −5° to −8° while a solution of 5.89 g (20.6 mmoles) of dimethyl 3,3-difluoro-2-oxo-n-nonylphonate in 45 ml of glyme was added dropwise over 1 hour; then 6.7 g (22.6 mmoles) of aldehyde 4d in 30 ml of glyme was added all at once and the mixture was stirred at room temperature for 2 hours. The mixture was concentrated under vacuum, mixed with 130 ml of water containing 15 g of NH4Cl, and extracted with ether. The ether was dried and evaporated and the crude product was purified by HPLC (1:1 EtOAc/hexane), affording pure, optically-active 8-azaprostanoid ketone 5d (TLC, R$_f$=0.5, 1:1 EtOAc/hexane), [α]$_D$+1.1°, [α]$_{405}$+20.8° (c=3.33, dioxane). The pmr spectrum confirmed the structure.

$^{19}$F nmr spectra of samples of these two 8-azaprostanoid ketones prepared similarly showed (CDCl3, F-11) proton-decoupled singlets at −107.46 ppm.

Optically active 8-azaprostanoid ketones 5l and 5d are each predominantly a single enantiomer. Their absolute configurations are believed to be represented by structures 5(R) for 5l and 5(S) for 5d.

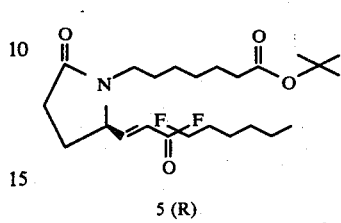
5 (R)

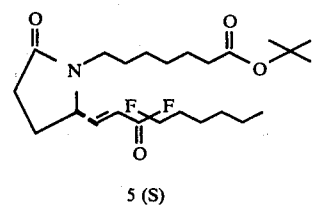
5 (S)

g. Optically active (l) tert-butyl 7-[2-oxo-5(R or S)5-(4,4-difluoro-3(R,S)-hydroxy-1n-dec-1(E)-enyl)-1-pyrrolidinyl]heptanoate[6l(15 R,S)] and optically active (d) tert-butyl 7-[2-oxo-5(S or R)5-(4,4-difluoro-3(R,S)-hydroxy-1n-dec-1(E)-enyl)-1-pyrrolidinyl]-heptanoate[6d(15 R,S)]

5l ⟶

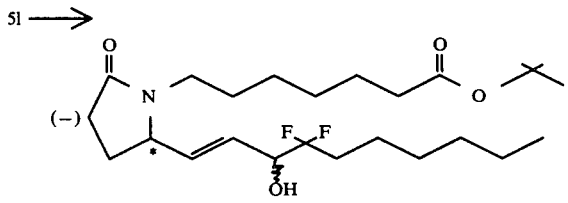
6l (15 R,S)

5d ⟶

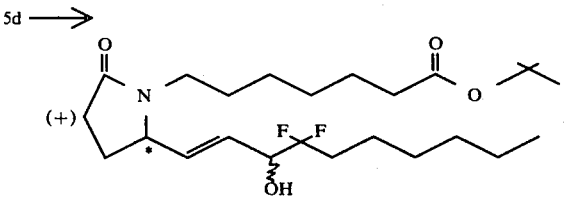
6d (15 R,S)

A mixture of 2.6 g of optically-active 8-azaprostanoid ketone 5l and 0.5 g of NaBH4 in 50 ml of ethanol was kept at −20° for 3.3 hrs and then poured into 500 ml of saturated NH4Cl solution and extracted with ethyl acetate. The ethyl acetate extract was dried (MgSO4/CaSO4) and evaporated giving the optically-active mixture of 8-azaprostanoids 6l (15R,S). Analysis by TLC (silica gel, EtOAc) showed this to be an approximately 50:50 mixture of the two (C-15 epimeric alcohols (R$_f$= ~0.5); analytical HPLC (5% ethanol in cyclopentane) showed a ratio of about 53/47 (less mobile isomer to more mobile isomer). HRMS showed a very weak 459 parent ion (M) and a stronger M—C4H9 ion C$_{21}$H$_{34}$O$_4$NF$_2$, calculated 402.2454, measured 402.2483; $^{19}$F nmr (CDCl3, TMS, F-11) shows two sets (2 diastereomeric) of AB patterns (proton decoupled) with each set of peaks centered at −107.18 (weak), −109.82

(strong), −111.26 (strong), −113.92 (weak) ppm. Specific rotations for another sample prepared similarly $[\alpha]_D-11.6°$, $[\alpha]_{365}-57.9°$ (c=3.33, EtOH).

In like manner, reduction of 0.8 g of ketone 5d by 0.15 g of NaBH$_4$ in 25 ml of ethanol at −20° for 5 hrs gave the optically-active mixture of 8-azaprostanoids 6d (15R,S); HRMS identical to that of 7l (15R,S); $[\alpha]_D+11.8°$, $[\alpha]_{365}+58.4°$ (c=3.33, EtOH).

EXAMPLE 44

Four optically-active isomers of tert-Butyl 7-[2-Oxo-5(R or S)-5-(4,4-difluoro-3(R or S)-3hydroxy-1-n-dec-1(E)-enyl)-1-pyrrolidinyl]heptanoate; 6l(15R), 6l(15S), 6d(15R), and 6d(15S).

Alcohols 6l(15R,S) being diastereomeric can be separated by chromatography. Likewise, alcohols 6d(15R,S) can be separated by chromatography. A particularly effective solvent system for these separations when they are carried out by HPLC on silica gel is 5% isopropyl alcohol in cyclopentane. In this manner alcohol 6l(15R,S) could be separated into optically active alcohols 6l(15R) and 6l(15S) and alcohol 6d(15R,S) could be separated into optically active alcohols 6d(15S) and 6d(15R). These four optically active alcohols are substantially single optical isomers with what are believed to be the following absolute configurations.

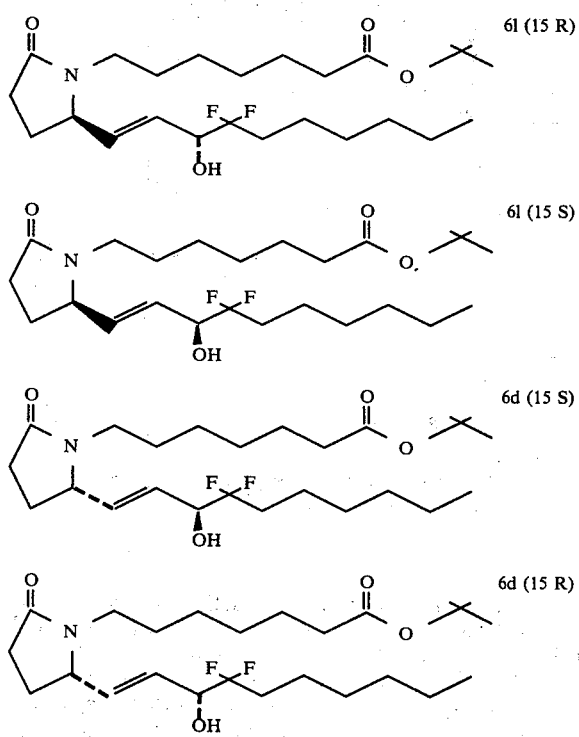

Alcohol 6l(15R) (the slower-moving diastereomer) had $[\alpha]_D+1.9°$, $[\alpha]_{365}-11.0°$ (c=3.33, ethanol); alcohol 6l(15S) (the faster-moving diastereomer) had $[\alpha]_D-29.7°$, $[\alpha]_{365}-122.4°$ (c=3.33, ethanol). Alcohol 6d(15S) (slower moving) had $[\alpha]_D-1.3°$, $[\alpha]_{365}+13.5°$ (c=3.33, ethanol) and alcohol 6d(15R) (faster moving) had $[\alpha]_D+28.0°$, $[\alpha]_{365}+114.8°$ (c=3.33, ethanol). The HRMS spectra of these four alcohols were essentially identical, and supported the molecular ion assignment C$_{25}$H$_{43}$O$_4$NF$_2$. The $^{19}$F nmr (CDCl$_3$, TMS, F-11) spectra confirmed both the structure of these alcohols and the fact that the diastereomeric components had been separated, since each show a single AB pattern (when proton decoupled); e.g. for 6l(15R) single peaks were found at −107.23 (weak), −109.86 (strong), −111.37 (strong) and −114.01 (weak) ppm and for 6l(15S) single peaks were found at −107.49 (weak), −110.14 (strong), −111.38 (strong), and −114.04 (weak) ppm.

EXAMPLE 45

Four optically-active isomers of 7-[2-Oxo-5(R or S)-5-(4,4-difluoro-3(R or S)-3-hydroxy-1n-dec-1(E)-enyl)-1-pyrrolidinyl]heptanoic Acid [7l(15R), 7l(15S), 7d(15S), and 7d(15R)].

A solution of 0.390 g of the tert-butyl ester 6l(15R) in 2 ml of tetrahydrofuran was added with stirring to 10 ml of 85% phosphoric acid cooled in an ice bath. The ice bath was then removed and the mixture stirred at ambient temperature for about 4 hours. It was then poured into 50 cc of saturated NaCl solution and extracted three times with ethyl acetate, which was dried and evaporated. Purification of the acid thus obtained by dissolving it in 5% NaHCO$_3$ and then regenerating it by acidification, gave 0.280 g of optically active 8-azaprostanoid acid 7l(15R). This acid is one, or substantially one, optical isomer. Treatment of the other optically active esters 6l(15S), 6d(15R), and 6d(15S) similarly with phosphoric acid gave the corresponding acids 7l(15S), 7d(15R), and 7l(15S), eac acid being one, or substantially one, optical isomer. The absolute configurations of these optically active acids are believed to be as indicated the following structures.

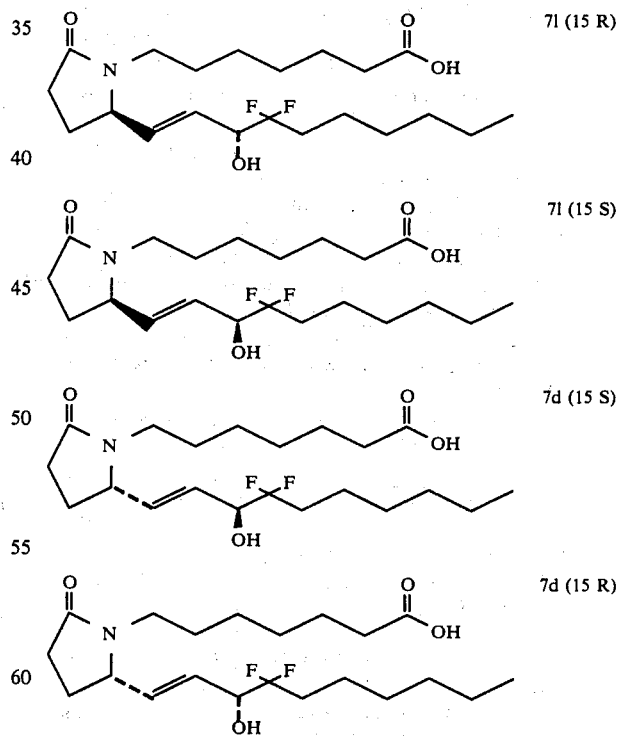

Thus, 7l(15R), a preferred compound of this invention, would be named as 7-[2-oxo-5(R)-5-(4,4-difluoro-3(R)-3-hydroxy-1n-dec-1(E)-enyl)-1-pyrrolidinyl]heptanoic acid and the other compounds of this group of four compounds would be named in similar manner.

EXAMPLE 46

Optically active (l) 7-[2-Oxo-5-(R or S)5-(4,4-difluoro-3(R,S)hydroxy-1n-dec-1(E)-enyl)-1-pyrrolidinyl]heptanoic Acid [7l(15R,S)] and optically-active (d) 7-[2-Oxo-5(S or R)5-(4,4-difluoro-3(R,s)-hydroxy-1n-dec-1(E)-enyl)-1-pyrrolidinyl]heptanoic Acid [7d(15R,S)]

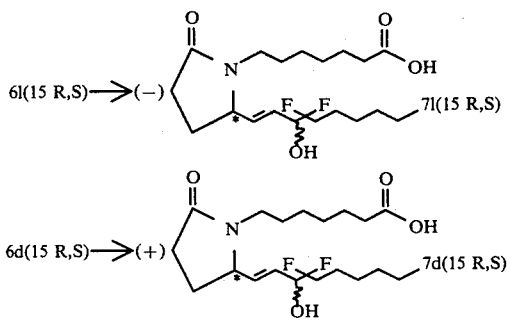

Instead of separating the diastereomers of optically active 8-azaprostanoid esters 6l(15R,S) and 6d(15R,S) as described in Example 45, these esters can be hydrolyzed directly to corresponding optically active acids that are mixtures of C-15 epimers. Thus, treatment of these esters in tetrahydrofuran with 85% phosphoric acid in a manner analogous of the procedure described in Example 45 gave optically active 8-azaprostanoid acids 7l(15R,S) and 7d(15R,S).

The absolute configurations of 7l(15R,S) and 7d(15R,S) are believed to be represented by the following structures,

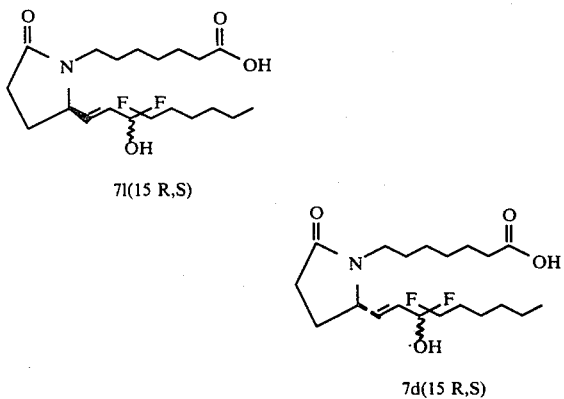

EXAMPLE 47 racemic tert-Butyl 7-[2-Oxo-5(RS)-5-(4,4-difluoro-3(RS)-hydroxy-4-phenyl-1n-but-1(E)-enyl)-1-pyrrolidinyl]heptanoate (21)

a. Dimethyl 3,3-Difluoro-2-oxo-3-phenyl-propylphosphonate (19)

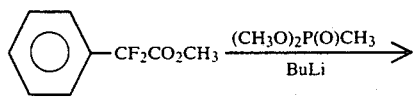

$\xrightarrow{\text{(CH}_3\text{O)}_2\text{P(O)CH}_3}{\text{BuLi}}$

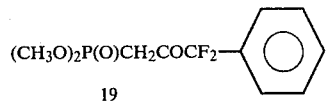

To a solution of 27.3 g (0.22 mole) of dimethyl methylphosphonate in 400 cc of dry tetrahydrofuran was added dropwise over 45–60 min 126 ml of 1.6 M (0.202 mole) of butyl lithium/hexane while keeping the reaction mixture at −72° to −78°. The reaction mixture was stirred for 20 min more with continued cooling and then 18.6 g (0.100 mole) of methyl α, α-difluorophenyl acetate in 25 ml of tetrahydrofuran was added dropwise over 25 min while keeping the reaction mixture at −72° to −78°. The mixture was stirred for 10 min with continued cooling and poured directly into 1 liter of saturated NaCl solution containing 25 ml of conc. HCl. The organic layer was drawn off and the aqueous layer was extracted twice with ether. The combined organic layers were washed once with satd. NaCl solution containing some HCl, dried over MgSO$_4$/CaSO$_4$, and evaporated, giving 31.8 g of oil. Distillation of this oil at about 105°/0.01 Torr gave 23.5 g of 19 (88%) as a colorless oil; $^{19}$F (CDCl$_3$, TMS, F-11) singlet at −105.81 ppm; HRMS m/e calculated for C$_{11}$H$_{13}$O$_4$F$_2$P: 278.0536, measured 278.0519.

b. racemic tert-Butyl 7-[2-Oxo-5(RS)-5-(4,4-difluoro-3-oxo-4-phenyl-1-but-1-(E)-enyl)-1-pyrrolidinyl]heptanoate (20)

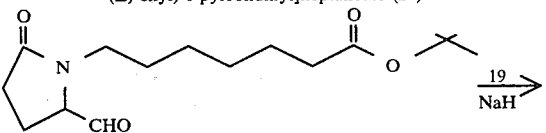

This reaction was carried out in a manner analogous to that used to prepare ketone 12 (Example 40, part c). A solution of 5.32 g (20 mmoles) of phosphonate ester 19 in 40 ml of glyme was added to 0.48 g (20 mmoles) of sodium hydride in 50 ml of glyme at 0°, and to the sodium salt thus obtained was added a solution of 6.52 g of aldehyde 4 in 20 ml of glyme. After being heated at reflux temperature, the mixture was worked up (as described for ketone 12), giving 8.58 g of crude 20. Purification by HPLC (EtOAc) gave 5.9 g of ester 20, which according to TLC (EtOAc) was about 95% pure (R$_f$=0.63); $^{19}$F nmr (CDCl$_3$, TMS, F-11) −107.29 ppm; pmr agreed showing 2 coupled vinyl protons (6.3–7.0 ppm) in an AB pattern with the lower field doublet split further into doublets; HRMS m/e for C$_{21}$H$_{25}$NO$_4$F$_2$ (M—C$_4$H$_8$) calculated: 393.1750, measured 393.1745.

20 →

39

-continued

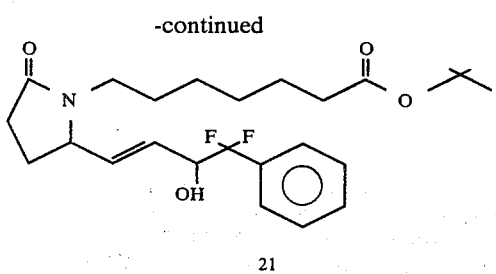

21

Reduction of 5.6 g of ketone 20 by 1.0 g of NaBH4 in 75 ml of ethanol at −20° for 2.75 hrs gave 3.94 g of alcohol 21 after purification by HPLC (EtOAc); HRMS m/e calculated for $C_{25}H_{35}NO_4F_2$: 451.2532, measured 451.2551; calculated for $M-C_4H_9O$: 378.1879, measured 378.1892.

EXAMPLE 48 racemic 7-[2-Oxo-5(RS)-4,4-difluoro-3(RS)-hydroxy-4-phenyl-1-but-1(E)enyl)-1-pyrrolidinyl]heptanoic Acid (22)

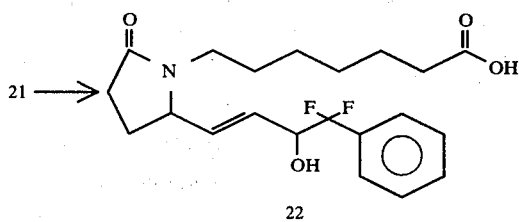

Hydrolysis of 3.5 g of the tert-butyl ester 21 in 4 ml of tetrahydrofuran and 35 ml of 85% $H_3PO_4$ for 3.5 hrs at room temperature and isolation of the product in a manner analogous to Example 41, gave about 1.5 g of acid 22; pmr (CDCl3, TMS) 7.3 (s, phenyl), 5.5 (2 peaks, broad, vinyl), 4.4 (t of d, J=12,2,=CH$\underline{CH}$(OH)CF2) $^{19}$F nmr (CDCl3, TMS, F-11) proton spin decoupled) 2 parts (2 diastereomers) of AB quarters centered at −107.47 ppm with 250 Hz between the weak-strong pairs of each of the two sets of quarters; HRMS m/e calculated for $C_{21}H_{27}NO_4F_2$: 395.1906, measured 395.1928.

The embodiments of the invention in which an exclusive property or privilege is claimed are defined as follows:

1. A compound of the formula

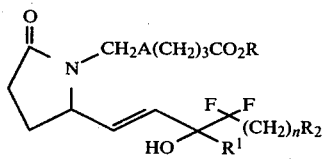

wherein
A is CH=CH (cis or trans), C≡C, or CH2CH2;
R is H, $C_1$-$C_{12}$ n-alkyl, branched chain alkyl, or cycloalkyl, or a physiologically acceptable metal or amine salt cation;
$R^1$ is H, CH3, or C2H5;
$R^2$ is CH3, CF3, phenyl, or mono- or disubstituted phenyl, the phenyl substituents being selected from the group F, Cl, CH3, OCH3, NO2, CF3;

40 n is an integer from 3 to 8 when $R^2$ is CH3 or CF3, or from 0 to 2 when $R^2$ is phenyl or substituted phenyl;
said compound selected from the group consisting of
 (i) a racemic mixture of stereo isomers,
 (ii) an optically active mixture of stereo isomers, and
 (iii) a single optically pure stereo isomer.

2. A compound according to claim 1 comprising a racemic mixture of stereo isomers.

3. A compound according to claim 1 comprising an optically active mixture of stereo isomers.

4. A compound according to claim 1 comprising a single optically pure stereo-isomer.

5. A compound according to claim 1:

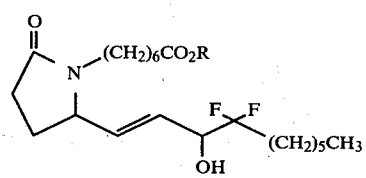

where R is selected from the group consisting of H, CH3, C2H5, tert-butyl, physiologically acceptable metal- and physiologically acceptable amine salt cation.

6. A compound according to claim 1:

where R is selected from the group consisting of H, CH3, C2H5, tert-butyl, physiologically acceptable metal- and physiologically acceptable amine salt cation.

7. A compound according to claim 1:

where R is selected from the group consisting of H, CH3, C2H5, tert-butyl, physiologically acceptable metal- and physiologically acceptable amine salt cation, and X is selected from the group consisting of H, F, Cl, CH3, OCH3, NO2, and CF3.

8. A compound according to claim 3:

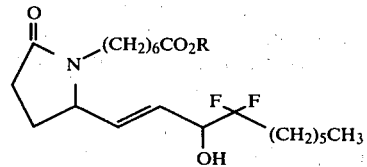

where R is selected from the group consisting of H, CH3, C2H5, tert-butyl, physiologically acceptable metal- and physiologically acceptable amine salt cation.

9. A compound according to claim 3:

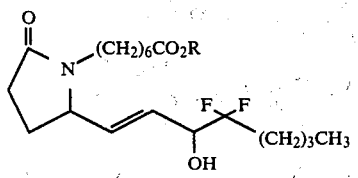

where R is selected from the group consisting of H, CH$_3$, C$_2$H$_5$, tert-butyl, physiologically acceptable metal- and physiologically acceptable amine salt cation.

10. A compound according to claim 3:

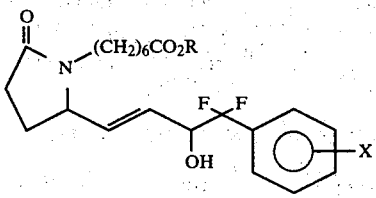

where R is selected from the group consisting of H, CH$_3$, C$_2$H$_5$, tert-butyl, physiologically acceptable metal- and physiologically acceptable amine salt cation, and X is selected from the group consisting of H, F, Cl, CH$_3$, OCH$_3$, NO$_2$, and CF$_3$.

11. A compound according to claim 4:

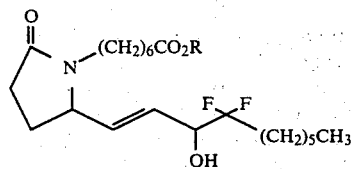

where R is selected from the group consisting of H, CH$_3$, C$_2$H$_5$, tert-butyl, physiologically acceptable metal- and physiologically acceptable amine salt cation.

12. A compound according to claim 4:

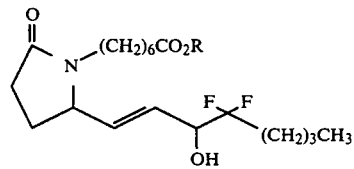

where R is selected from the group consisting of H, CH$_3$, C$_2$H$_5$, tert-butyl, physiologically acceptable metal- and physiologically acceptable amine salt cation.

13. A compound according to claim 4:

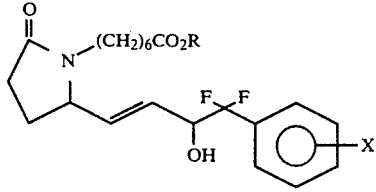

where R is selected from the group consisting of H, CH$_3$, C$_2$H$_5$, tert-butyl, physiologically acceptable metal- and physiologically acceptable amine salt cation, and X is selected from the group consisting of H, F, Cl, CH$_3$, OCH$_3$, NO$_2$, and CF$_3$.

14. A compound according to claim 8:

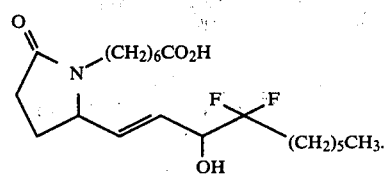

15. A compound according to claim 8:

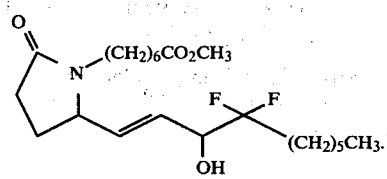

16. A compound according to claim 9:

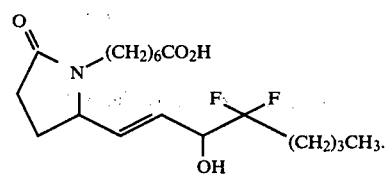

17. A compound according to claim 10:

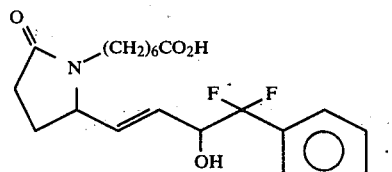

18. A compound according to claim 11:

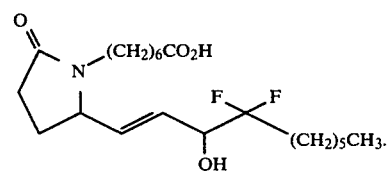

19. A compound according to claim 11 named 7-[2-oxo-5(R)-5(4,4-difluoro-3-(R)-3-hydroxy-1n-dec-1-(E)-enyl)-1pyrrolidinyl]heptanoic acid.

20. A compound according to claim 9 named 7-[2-oxo-5(R)-5(4,4-difluoro-3(R)-3-hydroxy-1-n-oct-1-(E)-enyl)-1-pyrrolidinyl]heptanoic acid.

21. A compound according to claim 11:

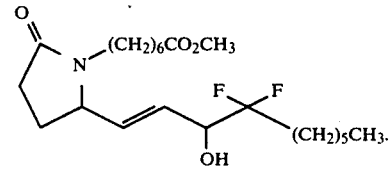

22. A compound according to claim 11:

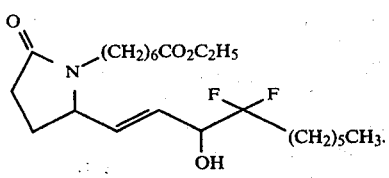

23. A physiologically acceptable metal salt of the compound according to claim 18.

24. A physiologically acceptable amine salt of the compound according to claim 18.

25. A compound according to claim 9:

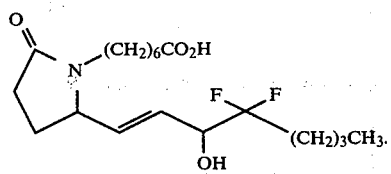

26. A compound according to claim 9:

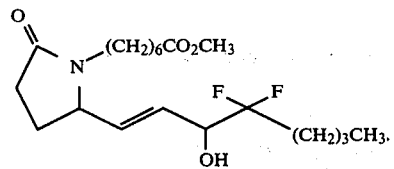

27. A compound according to claim 9:

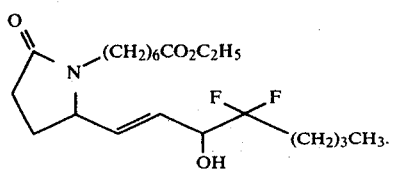

28. A physiologically acceptable metal salt of the compound according to claim 25.

29. A physiologically acceptable amine salt of the compound according to claim 25.

30. A pharmaceutical composition for treating gastrointestinal inflammation, peptic ulcers, asthma, or broncho-constriction in a human or an animal comprising an effective amount of a compound according to claim 1 with a pharmaceutically acceptable carrier.

31. A composition according to claim 30 in tablet form.

32. A composition according to claim 30 in capsule form.

33. A composition according to claim 30 in injectable form.

34. A composition according to claim 30 in aerosolizable form.

35. A method for preventing or treating a peptic ulcer in a human or an animal which comprises administering an effective amount of a pharmaceutical composition according to claim 30.

36. A method for controlling symptoms of bronchial asthma in a human which comprises administering an effective amount of a pharmaceutical composition according to claim 30.

37. A method for controlling symptoms of gastrointestinal ulcerative changes in a human or an animal which comprises administering an effective amount of a pharmaceutical composition according to claim 30.

* * * * *